(12) United States Patent
Spitz et al.

(10) Patent No.: US 12,180,244 B2
(45) Date of Patent: Dec. 31, 2024

(54) (THIO)NICOTINAMIDE RIBOFURANOSIDE SALTS AND COMPOSITIONS, METHODS OF MAKING, AND USES THEREOF

(71) Applicant: Biosynth AG, Staad (CH)

(72) Inventors: Urs Spitz, St. Gallen (CH); Günter Schabert, Goldbach (CH); Aysel Soydemir, Rorschach (CH); Lukas Wick, Winterthur (CH)

(73) Assignee: Biosynth AG, Staad (CH)

( * ) Notice: Subject to any disclaimer, the term of this patent is extended or adjusted under 35 U.S.C. 154(b) by 0 days.

(21) Appl. No.: 17/820,816

(22) Filed: Aug. 18, 2022

(65) Prior Publication Data

US 2023/0107185 A1    Apr. 6, 2023

Related U.S. Application Data

(62) Division of application No. 17/055,101, filed as application No. PCT/EP2019/062769 on May 17, 2019, now Pat. No. 11,447,514.

(30) Foreign Application Priority Data

May 18, 2018   (EP) .................................... 18173208

(51) Int. Cl.
  *C07H 1/06*   (2006.01)
  *C07H 19/048*   (2006.01)
(52) U.S. Cl.
  CPC ............ *C07H 1/06* (2013.01); *C07H 19/048* (2013.01); *C07B 2200/13* (2013.01)
(58) Field of Classification Search
  None
  See application file for complete search history.

(56) References Cited

U.S. PATENT DOCUMENTS

| | | |
|---|---|---|
| 2017/0146517 A1 | 5/2017 | Cohen et al. |
| 2018/0134742 A1* | 5/2018 | Migaud .................. C07H 19/20 |
| 2018/0134743 A1 | 5/2018 | Migaud et al. |

FOREIGN PATENT DOCUMENTS

| | | |
|---|---|---|
| CH | 318073 | 12/1956 |
| CN | 103709220 | 4/2014 |
| WO | WO-2004080410 | 9/2004 |
| WO | WO-2005070911 | 8/2005 |
| WO | WO-2015186068 | 12/2015 |
| WO | WO-2016014927 | 1/2016 |
| WO | WO-2016144660 | 9/2016 |
| WO | WO-2016149395 | 9/2016 |
| WO | WO-2017161165 | 9/2017 |
| WO | WO-2017218580 | 12/2017 |

OTHER PUBLICATIONS

Atkinson et al., 98. Synthesis of Glycosylpyridinium Compounds from Glycosylamines and from Glycosyl Halides, Journal of the Chemical Society 1965, pp. 610-615, XP055112149.
Broussy et al., The First Chemical Synthesis of the Core Structure of the Benzoylhydrazine-NAD Adduct, a Competitive Inhibitor of the *Mycobacterium tuberculosis* Enoyl Reductase, J. Org. Chem. 2005, vol. 70, No. 25, pp. 10502-10510, XP002496833.
International Search Report and Written Opinion for International Application No. PCT/EP2019/062769 dated Aug. 14, 2019. (12 pages).
Karrer et al., Kristallisiertes 3-Carbonsaureamid-N1-D-Ribosido-Pyridiniumbromid Und Verwandte Verbindungen, Biochimica et Biophysica Acta, vol. 12, 1953, pp. 51-55, XP023791571.
Lee et al., A chemical synthesis of nicotinamide adenine dinucleotide (NAD+), Chem. Commun., 1999, pp. 729-730, XP055103548.
Mishra et al., The role of microbial pullulan, a biopolymer in pharmaceutical approaches: A review, Journal of Applied Pharmaceutical Science 01 (06); 2011: 45-50.

* cited by examiner

*Primary Examiner* — Layla D Berry
(74) *Attorney, Agent, or Firm* — Sheppard Mullin Richter & Hampton LLP

(57) ABSTRACT

The present invention relates to crystalline (thio)nicotinamide ribofuranoside salts, methods of making such crystalline salts, a pharmaceutical composition comprising same, and use of said crystalline salts as nutritional (dietary) supplements. Furthermore, the present invention relates to a composition comprising amorphous (thio)nicotinamide ribofuranoside salts and its use as nutritional (dietary) supplement.

2 Claims, 9 Drawing Sheets

(THIO)NICOTINAMIDE RIBOFURANOSIDE SALTS AND COMPOSITIONS, METHODS OF MAKING, AND USES THEREOF

CROSS-REFERENCE TO RELATED APPLICATIONS

This application is a divisional of U.S. patent application Ser. No. 17/055,101, filed Nov. 12, 2020, now U.S. Pat. No. 11,447,514, which is a U.S. National Stage Application under 35 U.S.C. § 371 of International Application No. PCT/EP2019/062769, filed May 17, 2019, which application claims the benefit of European Application No. 18173208.2, filed May 18, 2018, all of which are hereby incorporated by reference in their entireties.

FIELD OF THE INVENTION

The present invention relates to crystalline (thio)nicotinamide ribofuranoside salts, methods of making such crystalline salts, a pharmaceutical composition comprising same, and use of said crystalline salts as nutritional (dietary) supplements. Furthermore, the present invention relates to a composition comprising amorphous (thio)nicotinamide ribofuranoside salts and its use as nutritional (dietary) supplement.

Furthermore, the present invention relates to a composition comprising (thio)nicotinamide ribofuranoside in amorphous form, a method of making same, and uses thereof as nutritional supplement or pharmaceutical composition.

BACKGROUND OF THE INVENTION

Nicotinamide riboside (nicotinamide-β-D-ribofuranoside; CAS Number 1341-23-7) is a precursor of nicotinamide adenine dinucleotide ($NAD^+$/NADH) and nicotinamide adenine dinucleotide phosphate ($NADP^+$/NADPH). In addition, nicotinamide riboside is a niacin (vitamin B3) equivalent. Nicotinamide riboside may be used in pharmaceutical compositions and nutritional supplements or as an intermediate product in the chemical synthesis of NAD (H) or NADP (H).

WO 2016/014927 discloses a crystalline form of nicotinamide riboside chloride which is described to have advantageous properties relative to amorphous forms, e.g. since it may be better purified compared to amorphous forms. The crystalline chloride salt is obtained from an amorphous chloride salt by re-crystallization in a polar solvent such as methanol.

Lee et al. (Chem. Commun., 1999, 729-730) disclose chemical synthesis of β-nicotinamide riboside bromide. The synthesis comprises conversion of tetraacetyl-β-D-ribofuranose to a 1.5:1 β:α mixture of sugar bromide intermediate compounds using hydrogen bromide in $CH_2Cl_2$ as bromination agent. Reaction of the sugar bromide intermediate compounds with nicotinamide in $SO_2$ at −10° C. followed by crystallization from 5:1 acetone-Bu$^t$OMe allegedly afforded acetylated nicotinamide riboside (β:α=25:1) in 90% yield.

According to an alternative approach described in Lee et al., a 3.3:1 (β:α) anomeric mixture was obtained when acetonitrile was used instead of $SO_2$ in the glycosylation step, and the pure β-anomer of acetylated nicotinamide riboside was allegedly selectively crystallized in 65% yield from the reaction mixture (−15° C.). Furthermore, deacetylation (i.e. deprotection) with ammonia in methanol followed by crystallization is reported to give crystalline β-nicotinamide bromide salt in 80% isolated yield.

Despite these efforts in the art, the conventional manufacturing methods of nicotinamide riboside are costly, not suited for nicotinamide riboside production on an industrial scale, and/or do not yield the required product quality, in particular in terms of product purity.

OBJECTS OF THE INVENTION

In view of the above, there is a need in the art for β-nicotinamide riboside salts of high purity which can be prepared at low costs and on an industrial scale.

SUMMARY OF THE INVENTION

The present inventors unexpectedly found that the process of producing β-(thio)nicotinamide ribofuranoside can be improved, e.g. by using appropriate bromination agents, deprotecting agents, and/or specific reaction conditions such as purification/crystallization conditions, resulting in a cost-efficient production of crystalline bromide or chloride salts of β-(thio)nicotinamide ribofuranoside compounds as well as further salts of pharmaceutically acceptable anions like sulfate and phosphate with high purity and in high yields on an industrial scale.

According to a first aspect, the present invention relates to a method of making crystalline nicotinamide-β-D-ribofuranoside bromide of formula O-Ia

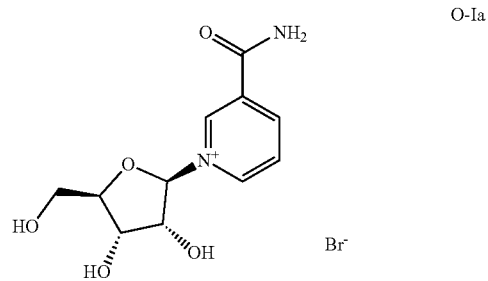

or crystalline thionicotinamide-β-D-ribofuranoside bromide of formula S-Ia

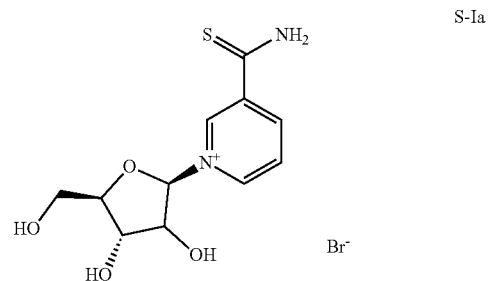

comprising at least step (A):
(A) subjecting a tetra-O-acyl-β-D-ribofuranose of formula II

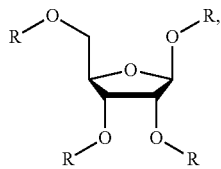

wherein each R is independently selected from acyl and wherein each R is preferably acetyl, to hydrogen bromide in acetic acid to yield a tri-O-acyl-β-D-ribofuranoside bromide of formula III

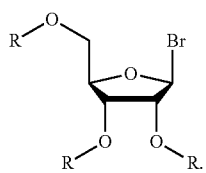

The method of the present invention may further comprise the following step (B):
(B) reacting the compound of formula III with nicotinamide of formula O-IV

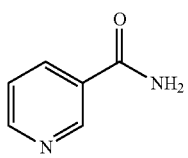

to obtain a nicotinamide-2,3,5-tri-O-acyl-β-D-ribofuranoside bromide of formula O-Va:

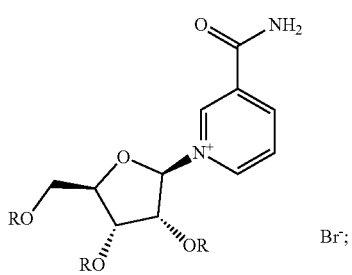

or reacting the compound of formula III with thionicotinamide of formula S-IV

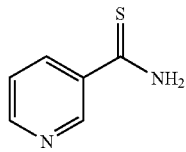

to obtain a thionicotinamide-2,3,5-triacyl-β-D-ribofuranoside bromide of formula S-Va:

Furthermore, the method of the present invention may comprise the following step (D):
(D) deprotecting the compound of formula O-Va or formula S-Va obtained in step (B), or obtained in optional step (C) of purifying the compound of formula O-Va or formula S-Va obtained in step (B), by removing the R groups using hydrogen bromide in acetic acid to give the compound of formula O-Ia or formula S-Ia.

According to a second aspect, the present invention relates to a method of making a crystalline nicotinamide-β-D-ribofuranoside salt or a crystalline thionicotinamide-β-D-ribofuranoside salt, wherein the anion of the salt is a pharmaceutically acceptable anion, particularly chloride, sulfate and phosphate, the method comprising:
(I) making a crystalline nicotinamide-β-D-ribofuranoside bromide of formula O-Ia or a crystalline thionicotinamide-β-D-ribofuranoside bromide of formula S-Ia according to a method of the first aspect; and subsequently subjecting the nicotinamide-β-D-ribofuranoside bromide of formula O-Ia or the thionicotinamide-β-D-ribofuranoside bromide of formula S-Ia to ion exchange using an ion exchanger loaded with said pharmaceutically acceptable anion; or
(II) making a crystalline nicotinamide-2,3,5-tri-O-acyl-β-D-ribofuranoside bromide of formula O-Va or a crystalline thionicotinamide-2,3,5-tri-O-acyl-β-D-ribofuranoside bromide of formula S-Va according to a method as described herein (e.g. step (B), or step (B) and step (A), or step (B) and step (A) and step (C), of the method of the first aspect), and deprotecting the compound of formula O-Va or formula S-Va in the presence of a pharmaceutically acceptable anion and protons; and subsequently subjecting the formed product to ion exchange using an ion exchanger loaded with said pharmaceutically acceptable anion; or
(III) making a crystalline nicotinamide-2,3,5-tri-O-acyl-β-D-ribofuranoside bromide of formula O-Va or a crystalline thionicotinamide-2,3,5-tri-O-acyl-β-D-ribofuranoside bromide of formula S-Va according to a method as described herein (e.g. step (B), or step (B) and step (A), or step (B) and step (A) and step (C), of the method of the first aspect), and subjecting the compound of formula O-Va or formula S-Va to ion-exchange with a pharmaceutically acceptable anion using an ion exchanger loaded with said pharmaceutically acceptable anion; and subsequently deprotecting the formed ion exchanged product in the presence of protons and said pharmaceutically acceptable anion.

According to a third aspect, the present invention relates to a crystalline nicotinamide-2,3,5-tri-O-acetyl-β-D-ribofuranoside bromide of formula O-Va, wherein R is acetyl, characterized by a powder X-ray diffraction pattern as defined in FIG. 1 herein below; or a crystalline nicotinamide-β-D-ribofuranoside bromide of formula O-Ia characterized by a powder X-ray diffraction pattern as defined in FIG. 2 herein below; or a crystalline nicotinamide-2,3,5-tri-O-acetyl-β-D-ribofuranoside chloride of formula O-Vb, wherein R is acetyl, characterized by a powder X-ray diffraction pattern as defined in FIG. 3 herein below; or a crystalline nicotinamide-β-D-ribofuranoside chloride of formula O-Ib characterized by a powder X-ray diffraction pattern as defined in FIG. 4 herein below; or a crystalline thionicotinamide-2,3,5-tri-O-acetyl-β-D-ribofuranoside bromide of formula S-Va, wherein R is acetyl, characterized by a powder X-ray diffraction pattern as defined in FIG. 5 herein below; or a crystalline thionicotinamide-β-D-ribofuranoside bromide of formula S-Ia characterized by a powder X-ray diffraction pattern as defined in FIG. 6 herein below; or a crystalline thionicotinamide-β-D-ribofuranoside chloride of formula S-Ib characterized by a powder X-ray diffraction pattern as defined in FIG. 7 herein below; or a crystalline thionicotinamide-2,3,5-tri-O-acetyl-β-D-ribofuranoside chloride of formula S-Vb characterized by a powder X-ray diffraction pattern as defined in FIG. 8 herein below.

The third aspect of the present invention further relates to a crystalline nicotinamide-β-D-ribofuranoside bromide of formula O-Ia or a crystalline thionicotinamide-β-D-ribofuranoside bromide of formula S-Ia, obtainable by a method of the first aspect; or a crystalline nicotinamide-β-D-ribofuranoside salt or a crystalline thionicotinamide-β-D-ribofuranoside salt, wherein the anion of the salt is a pharmaceutically acceptable anion (i.e. not bromide), such as chloride, sulfate and phosphate, obtainable by a method of the second aspect.

According to a fourth aspect, the present invention relates to the use of a crystalline nicotinamide-β-D-ribofuranoside salt or a crystalline thionicotinamide-β-D-ribofuranoside salt of the third aspect as nutritional supplement. Furthermore, the fourth aspect also relates to a pharmaceutical composition comprising said crystalline nicotinamide-β-D-ribofuranoside salt or said crystalline thionicotinamide-β-D-ribofuranoside salt.

According to a fifth aspect, the present invention relates to a method of making a composition comprising an amorphous nicotinamide-β-D-ribofuranoside salt or an amorphous thionicotinamide-β-D-ribofuranoside salt, wherein the anion of the salt is a pharmaceutically acceptable anion, particularly chloride, sulfate and phosphate, and a carrier, the method comprising making a crystalline nicotinamide-β-D-ribofuranoside salt or a crystalline thionicotinamide-β-D-ribofuranoside salt according to a method of the second aspect, and further comprising step (F), and optionally step (G):

(F) contacting the salt with a carrier, e.g. pullulan, and one or more solvents;
(G) removing the one or more solvents from the mixture obtained in step (F) to obtain a solid form of the composition in which the nicotinamide-β-D-ribofuranoside salt or thionicotinamide-β-D-ribofuranoside salt is present in amorphous form.

According to a sixth aspect, the present invention relates to a composition comprising a nicotinamide-β-D-ribofuranoside salt or a thionicotinamide-β-D-ribofuranoside salt, wherein the anion of the salt is a pharmaceutically acceptable anion, particularly chloride, sulfate and phosphate, and a carrier, wherein said nicotinamide-β-D-ribofuranoside salt and said thionicotinamide-β-D-ribofuranoside salt are amorphous. Preferably, the composition is prepared by a method according to the fifth aspect.

The composition according to the sixth aspect may be used for the same applications or uses as defined in the fourth aspect, i.e. as nutritional supplement or as pharmaceutical ingredient, e.g. in a pharmaceutical composition that optionally comprises a carrier such as pullulan.

According to a seventh aspect, the present invention relates to a method of making a tri-O-acyl-β-D-ribofuranoside bromide of formula III

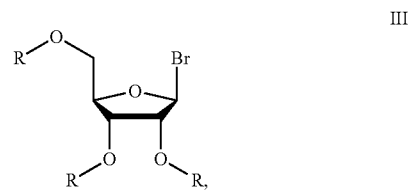

the method comprising step (α):
(α) subjecting a tetra-O-acyl-β-D-ribofuranoside of formula II

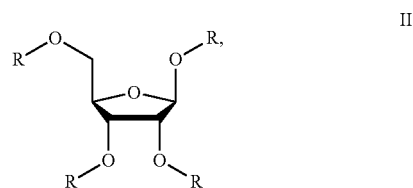

wherein each R is independently selected from acyl and wherein each R is preferably acetyl, to hydrogen bromide in acetic acid.

According to an eighth aspect, the present invention relates to a method of removing acyl groups, in particular acetyl groups, from a nicotinamide-2,3,5-tri-O-acyl-β-D-ribofuranoside bromide of formula O-Va or a nicotinamide-2,3,5-tri-O-acyl-β-D-ribofuranoside chloride of formula O-Vb

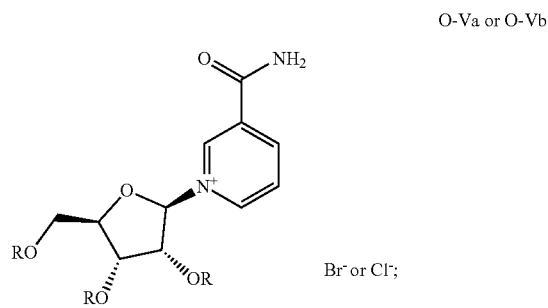

or from a thionicotinamide-2,3,5-tri-O-acyl-β-D-ribofuranoside bromide of formula S-Va or a thionicotinamide-2,3,5-tri-O-acyl-β-D-ribofuranoside chloride of formula S-Vb

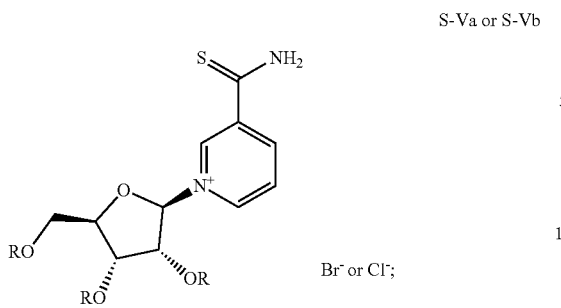

wherein each R is independently selected from acyl and wherein each R is preferably acyl, the method comprising at least step (i) or (ii):
(i) reacting the compound of formula O-Va or formula S-Va with hydrogen bromide in acetic acid;
(ii) reacting the compound of formula O-Va or formula S-Va with hydrogen chloride in methanol.
Further embodiments are set forth in the appended claims.

BRIEF DESCRIPTION OF THE FIGURES

The present invention is further described by the appended figures, in which.

DETAILED DESCRIPTION OF THE INVENTION

Figure 1:
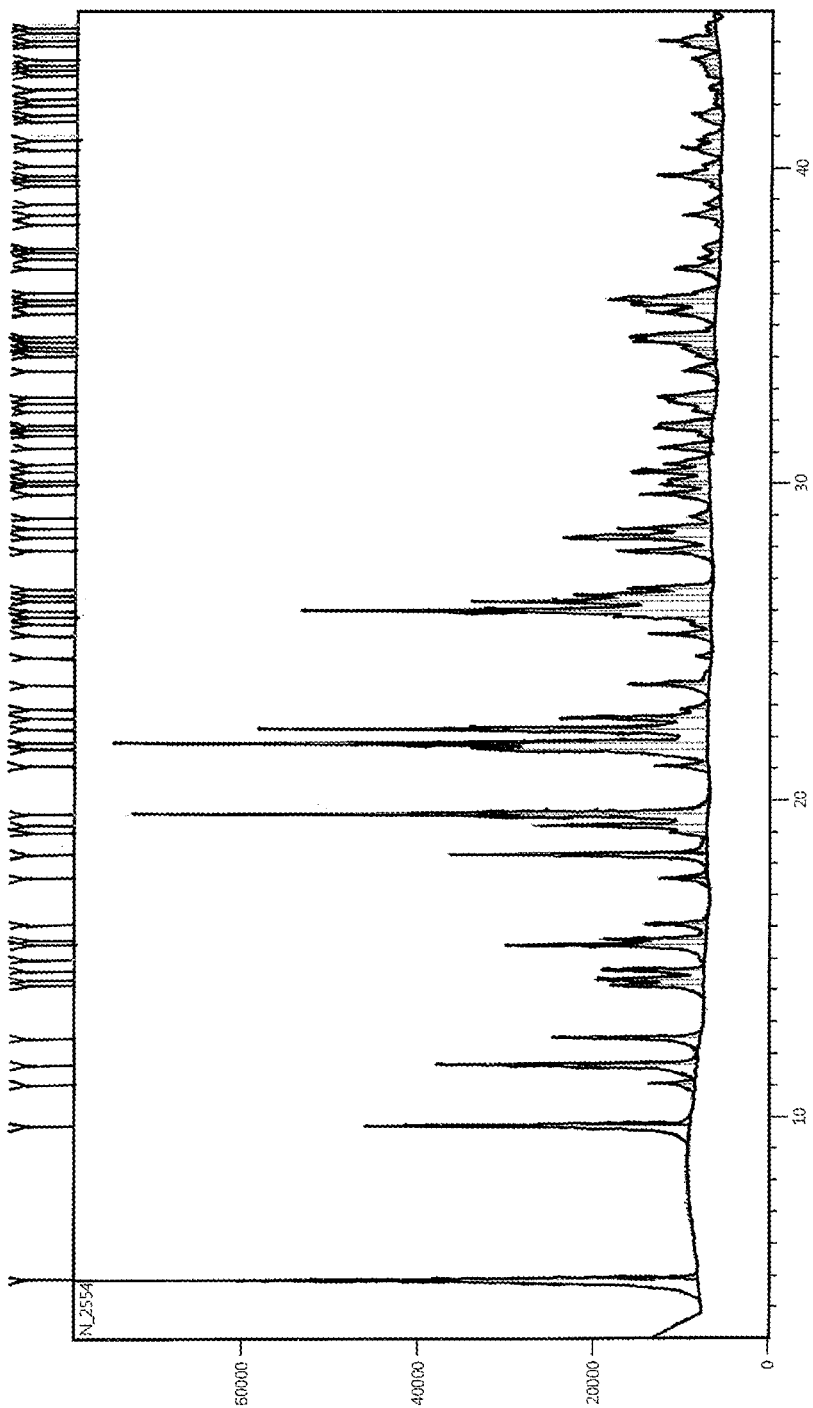
FIG. 1 shows a powder X-ray pattern of crystalline nicotinamide-2,3,5-tri-O-acetyl-β-D-ribofuranoside bromide of formula O-Va (R=acetyl)

The various aspects of the present invention will now be described in more detail with reference to the figures.

Method of Making Crystalline
(Thio)Nicotinamide-β-D-Ribofuranoside Bromide
O-Ia or S-Ia (First Aspect)

According to a first aspect, the invention relates to a method of making crystalline nicotinamide-β-D-ribofuranoside bromide of formula O-Ia

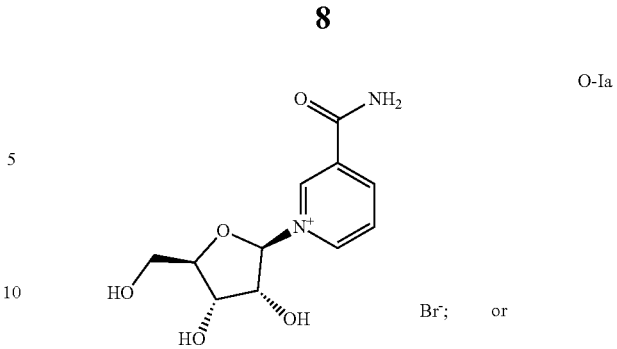

a crystalline thionicotinamide-β-D-ribofuranoside bromide of formula S-Ia

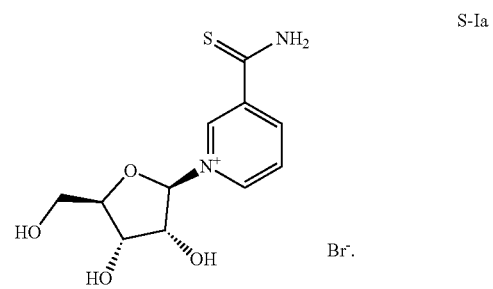 [SMILES: NC(=S)c1ccc[n+]([C@@H]2O[C@H](CO)[C@@H](O)[C@H]2O)c1]

As used herein, the term "(thio)nicotinamide" encompasses the term "nicotinamide" and "thionicotinamide" such as nicotinamide-β-D-ribofuranoside and thionicotinamide-β-D-ribofuranoside.
The method according to the invention comprises at least step (A):
(A) subjecting a tetra-O-acyl-β-D-ribofuranose of formula II,

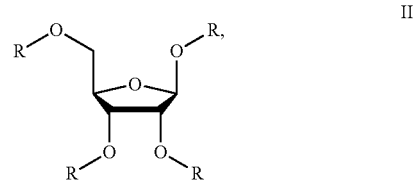

wherein each R is independently an acyl group, to hydrogen bromide in acetic acid to yield a tri-O-acyl-β-D-ribofuranoside of formula III:

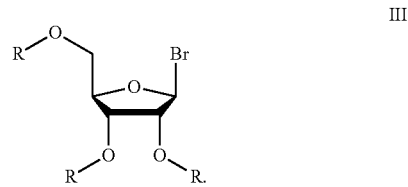

The term "acyl" as synonymously used with the term "acyl group" in the compound of formula II means that the acyl group may be independently selected from alkyl carbonyl, aryl carbonyl or heteroaryl carbonyl.
The term "alkyl carbonyl" is synonymously used with the term "alkanoyl".

In one embodiment, R is independently selected from alkyl carbonyl, aryl carbonyl and heteroaryl carbonyl, preferably from $C_{1-10}$ alkyl carbonyl and benzoyl, and is preferably acetyl.

In one embodiment, acyl may be substituted.

In one embodiment, acyl may be independently substituted with one or more of the following substituents: $C_{1-6}$ alkyl, $C_{1-6}$ alkoxy, $C_{1-6}$ thioalkyl, halogen, nitro, cyano, $NH(C_{1-6}$ alkyl), $N(C_{1-6}$ alkyl)$_2$, and $SO_2N(C_{1-6}$ alkyl)$_2$.

In one embodiment, acyl is $C_{1-6}$ alkanoyl such as formyl, acetyl, propionyl, butyryl, valeryl or cyclohexyl, optionally substituted with one or more of the substituents mentioned above.

In another embodiment, acyl is benzoyl or naphthoyl, preferably benzoyl, optionally substituted with one or more of the substituents mentioned above.

Tetra-O-acyl-β-D-ribofuranoses of formula II are either known compounds or may be prepared according to known methods.

In a preferred embodiment, commercially available tetra-O-acetyl-β-D-ribofuranose (CAS Number 13035-61-5)

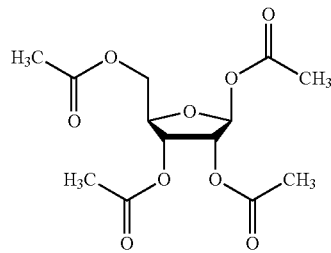

is used in step (A).

Thus, R is preferably acetyl.

Hydrogen bromide in acetic acid, preferably glacial acetic acid, as used in step (A) is commercially available. A preferred composition comprises 33% by weight of hydrogen bromide in glacial acetic acid (CAS Number 37348-16-6).

Preferably, the reaction is carried out in an aprotic polar solvent, preferably a nitrile. In a preferred embodiment, acetonitrile is used as solvent in which the compound of formula II is dissolved or suspended prior to the addition of hydrogen bromide in acetic acid.

The reaction temperature is advantageously kept in a temperature range of from −10 to 10° C. such as −5 to 5° C. in order to control the slightly exothermic reaction of compound II with hydrogen bromide in acetic acid.

The compound of formula III may be isolated from the reaction mixture by evaporating the solvent and acetic acid.

However, the inventors of the present invention discovered that an evaporation of solvent and acetic acid on an industrial scale in commonly used reactors may significantly negatively affect the properties of the resulting tri-O-acyl-β-D-ribofuranoside bromide of formula III in terms of yield due to degradation and side-reactions such as epimerization or ring opening.

Furthermore, the subsequent reaction in step (B) with nicotinamide of formula O-IV or thionicotinamide of formula S-IV (nicotinamide O-IV, CAS Number 98-92-0; thionicotinamide S-IV, CAS Number 4621-66-3) to the desired crystalline nicotinamide-2,3,5-tri-O-acyl-β-D-ribofuranoside bromide of formula O-Va or thionicotinamide-2,3,5-tri-O-acyl-β-D-ribofuranoside bromide of formula S-Va as defined below is severely hampered, respectively the isolation of a crystalline product is not possible at all.

Therefore, the inventors investigated whether the crude product obtained in step (A), i.e. a product containing tri-O-acyl-β-D-ribofuranoside bromide of formula III, acetic acid and hydrogen bromide, may be reacted with (thio)nicotinamide IV in the subsequent step (B). It was expected that due to the reduced nucleophilicity of (thio)nicotinamide IV as a consequence of salt formation of (thio)nicotinamide IV with acetic acid the substitution of bromide in tri-O-acyl-β-D-ribofuranoside bromide of formula III by nicotinamide of formula O-IV or thionicotinamide of formula S-IV would be hampered or even fail.

The inventors of the present invention discovered that—contrary to expectation—the reaction mixture obtained in step (A) may be used for substituting bromide in tri-O-acyl-β-D-ribofuranoside bromide of formula III in good yield by (thio)nicotinamide IV. This was unexpected and thus surprising.

Without being bound by theory, it is believed that the reduced nucleophilicity of (thio)nicotinamide of formula IV upon acetate formation due to the presence of acetic acid in step (B), when the crude product obtained in step (A) is used for substituting bromide in tri-O-acyl-β-D-ribofuranoside bromide of formula III, is still sufficient in order to effect substitution: It further contributes to a smooth reaction with tri-O-acyl-β-D-ribofuranoside bromide of formula III such that side-reactions, e.g. ring opening reactions, epimerization or degradation reactions, are avoided as far as possible. This promotes the formation of a crystallized acylated product of formula Va, i.e. nicotinamide-2,3,5-tri-O-acyl-β-D-riboside bromide of formula O-Va or thionicotinamide-2,3,5-tri-O-acyl-β-D-riboside bromide of formula S-Va.

This unexpected finding has been proven to be of crucial importance for a successful up-scaling of the reaction to an industrial scale.

Therefore, in a preferred embodiment, the compound of formula III formed in step (A) is not isolated, but is employed in the next step (B) of the method according to the invention as the crude product, i.e. is used as the product which is contained in the reaction mixture obtained in step (A).

Thus, in one embodiment, the next step (B) in the method according to the invention is carried out using (thio)nicotinamide IV in form of its acetate.

In another embodiment, preferably the crude reaction mixture obtained in step (A) is used comprising the (thio)nicotinamide and acetic acid, respectively a composition comprising at least a portion of the reaction mixture obtained in step (A).

Accordingly, the method further comprises the following step (B):

(B) reacting a tri-O-acyl-β-D-ribofuranoside bromide of formula III with nicotinamide of formula O-IV

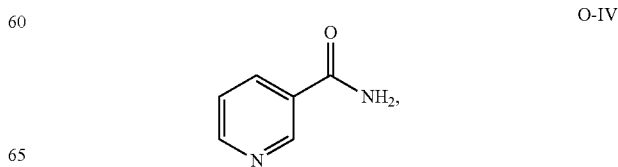

respectively with thionicotinamide of formula S-IV

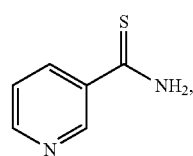

S-IV to yield a nicotinamide-2,3,5-tri-O-acyl-β-D-ribofuranoside bromide of formula O-Va:

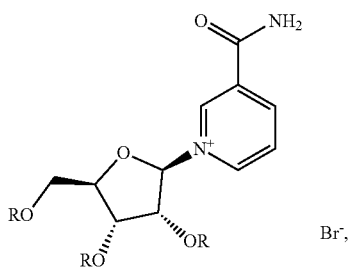

O-Va respectively a thionicotinamide-2,3,5-tri-O-acyl-β-D-riboside bromide of formula S-Va

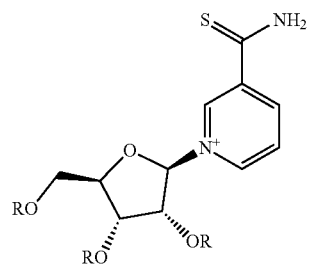

S-Va

In a preferred embodiment, nicotinamide O-IV, respectively thionicotinamide S-IV, is used in an excess compared to tri-O-acyl-β-D-ribofuranoside bromide of formula III.

Furthermore, and advantageously, nicotinamide of formula O-IV, respectively thionicotinamide of formula S-IV, is used in an amount sufficient—due to its basic properties—to neutralize an excess of hydrogen bromide and acetic acid still contained in the reaction mixture formed in step (A). The resulting salts (thio)nicotinamide bromide and/or acetate precipitate from the reaction mixture and may simply be separated off by filtration.

The resulting filtrate contains intermediate (thio)nicotinamide-2,3,5-tri-O-acyl-β-D-ribofuranoside bromide of formula Va, and only a comparatively small amount of (thio)nicotinamide IV if the excess of (thio)nicotinamide IV is chosen appropriately.

Since the compound of formula III is provided in the form of a mixture of anomers, also (thio)nicotinamide-2,3,5-tri-O-acyl-β-D-ribofuranoside bromide of formula Va is formed as a mixture of anomers.

The intermediate compound of formula Va is typically produced as a mixture of anomers β:α in a ratio of from about 5:1 to 6:1. This is an improvement over the method disclosed in the Lee-reference discussed above, where the similar reaction provided for a less favorable ratio of 3.3:1 of a β:α mixture of anomeric nicotinamide-2,3,5-tri-O-acyl-β-D-ribofuranoside bromides.

This favorable ratio of β:α anomer in the intermediate compound of formula V hypothesizes that also tri-O-acyl-β-D-ribofuranoside bromide of formula III is typically produced as a mixture of anomers β:α in a ratio range from about 5:1 to 6:1. This would be an additional improvement over the method disclosed in the Lee-reference discussed above, where the analogous reaction using hydrogen bromide in dichloromethane for making tri-O-acyl-β-D-ribofuranoside bromide of formula III provided for a less favorable ratio of 1.5:1 in terms of a β:α mixture of anomeric sugar bromides.

The inventors discovered that a successful large-scale reaction is possible only under the specific conditions indicated below.

In particular, the inventors discovered that besides the use of (thio)nicotinamide acetate for the substitution of bromide in tri-O-acyl-β-D-ribofuranoside bromide of formula III, also the use of an excess of nicotinamide of formula O-IV or thionicotinamide of formula S-IV adapted to the amount of hydrogen bromide used in the bromination step (A), is of crucial importance for carrying out the reaction in the large scale.

Since hydrogen bromide is used in a slight molar excess in the bromination reaction in step (A) relative to acyl compound of formula II (approx. 1.2 mole hydrogen bromide to 1 mole of compound of formula II), also (thio)nicotinamide of formula IV should be used in an appropriate excess in step (B) in order to neutralize said hydrogen bromide still being contained in the reaction mixture since said hydrogen bromide otherwise would negatively affect glycosylation. This may be seen in a reduced yield of the compound of formula Va if the reaction is carried out in absence of an excess of (thio)nicotinamide of formula IV.

Furthermore, surprisingly, the filtrate contains despite said excess of (thio)nicotinamide of formula IV only small amounts thereof, which facilitates the spontaneous crystallization of the substantially pure compound of formula O-Va, respectively S-Va, from acetone.

Accordingly, in a preferred embodiment, the molar ratio of hydrogen bromide to acyl compound of formula II used in step (A) is selected such to range from 1.1:1 to 1.3:1, wherein the molar ratio of (thio)nicotinamide of formula IV used in step (B) to hydrogen bromide used in step (A) is in the range of from 1.05:1 to 1.2:1.

In a further preferred embodiment, the molar ratio of hydrogen bromide to acyl compound of formula II used in step (A) is selected such to range from 1.15:1 to 1.25:1, wherein the molar ratio of (thio)nicotinamide of formula IV used in step (B) to hydrogen bromide used in step (A) is in the range of from 1.1:1 to 1.15:1.

Furthermore, it is advantageous to carry out step (B) such that a heated solution of (thio)nicotinamide of formula IV in acetonitrile is added to a cooled solution comprising tri-O-acyl-β-D-ribofuranoside bromide of formula III and a solvent, preferably acetonitrile.

Without being bound by theory, it is believed that under said conditions glycosylation is advantageously faster that the competing degradation of tri-O-acyl-β-D-ribofuranoside bromide of formula III.

Accordingly, in a preferred embodiment, step (B) is carried out such that (thio)nicotinamide of formula IV dissolved in acetonitrile is added to a solution comprising tri-O-acyl-β-D-ribofuranoside bromide of formula III and acetonitrile, hydrogen bromide and acetic acid, wherein the temperature of the solution of (thio)nicotinamide of formula IV in acetonitrile is kept in a range of from 50° C. to 75° C., and the temperature of the solution comprising tri-O-acyl-β-D-ribofuranoside bromide of formula III is kept in a temperature range of from −10° C. to 30° C.

In a preferred embodiment, the temperature of the solution of (thio)nicotinamide of formula IV in acetonitrile is kept in a range of from 70° C. to 75° C. and the temperature of the solution comprising tri-O-acyl-β-D-ribofuranoside bromide of formula III is kept in a temperature range of from 0° C. to 20° C.

After filtering the precipitated (thio)nicotinamide hydrobromide, respectively acetate, and after evaporating the solvent, preferably acetonitrile, the compound of formula Va (O-Va or S-Va) may be isolated.

Although the crude product may be employed in the next step, it is advantageous to purify and crystallize the compound of formula Va. Using a purified and crystallized compound of formula Va in the deprotecting step of the method according to the invention, i.e. step (D), improves the tendency of the target compound of formula Ia, either O-Ia or S-Ia, to result in a crystallized and thus in a substantially pure form.

Preferably, the compound of formula Va may be re-crystallized from acetone. The pure β-anomer is obtained.

Accordingly, in one embodiment, the method further comprises step (C):

(C) purifying the product obtained in step (B).

Preferably, purification according to step (C) is crystallization or re-crystallization.

The yield over steps (B) and (C) is typically in the range of from 40 to 50%.

In the next step of the method according to the invention, the acyl groups in the product obtained in step (B) or (C) are cleaved, i.e. the protected hydroxyl groups are deprotected.

Basically any method known in the art may be used to remove the acyl groups from the protected OH-groups.

In one embodiment, ammonia such as ammonia in methanol may be used for deprotection as disclosed in the above-discussed Lee reference. The inventors of the present invention can confirm the respective disclosure in said Lee-reference that this method cannot easily be repeated on a large scale and that the extent of cleavage may largely depend on the initial concentration and the total amount of ammonia in the reaction mixture. Moreover, unfavorable epimerization and degradation products resulting in brownish products may be observed which may negatively affect the formation of the target compound of formula Ia, either of formula O-Ia or of formula S-Ia, in crystallized form.

The inventors of the present invention discovered that cleavage may be advantageously performed with hydrogen bromide in acetic acid without the addressed drawbacks.

The reaction may be carried out in the presence of a solvent. A preferred solvent is methanol.

Accordingly, the method further comprises step (D):

(D) deprotecting the compound of formula Va, i.e. either of formula O-Va or of formula S-Va, obtained in step (B) or (C) by removing the R groups using hydrogen bromide in acetic acid to give the compound of formula Ia, i.e. either of formula O-Ia or of formula S-Ia.

This reaction may be beneficially carried out also at a large scale.

Since the deprotection reaction is slightly exothermic, it is preferred to control the reaction temperature. In a preferred embodiment, the temperature is kept in a range of from −5° C. to 25° C. such as 0° C. to 20° C.

In one embodiment, after cleavage of the acyl groups, i.e. the deprotection step, acetic acid and formed acids stemming from the acyl residues may be distilled off in vacuum, if desired.

The formed target compound of formula O-Ia or of formula S-Ia frequently directly precipitates from the solution obtained in the deprotection step in the form of crystals.

If necessary, crystallization may be promoted by the addition of seeding crystals.

The crystallized product O-Ia or S-Ia may be obtained in a purity of more than 97%, i.e. nearly free from the α-anomer, and containing only minor amounts of (thio)nicotinamide of formula IV which has been used for substituting bromide in tri-O-acyl-β-D-ribofuranoside bromide of formula III, respectively for neutralizing an excess of hydrogen bromide.

If further necessary, compound of formula O-Ia or of formula S-Ia may be further purified, preferably by re-crystallization. A suitable solvent is e.g. methanol.

In a preferred embodiment, the method further comprises step (E):

(E) purifying the product obtained in step (D).

In a preferred embodiment, purification according to step (E) comprises or is crystallization or re-crystallization.

The yield over steps (D) and (E) is typically in the range of from 60 to 70%.

The compound of formula Ia (O-Ia or S-Ia) may be transferred to the chloride Ib (O-Ib or S-Ib), if desired, since the chloride typically is pharmaceutically more acceptable than the bromide.

Advantageously, other crystalline salts in which the anion is a pharmaceutically acceptable anion may be prepared starting from the bromide of formula Ia. Preferably, sulfates and phosphates may be prepared.

Method of Making a Crystalline
(Thio)Nicotinamide-β-D-Ribofuranoside Chloride
or Another Pharmaceutically Acceptable Salt
(Second Aspect)

According to a second aspect, the invention relates to a method of making a crystalline nicotinamide-β-D-ribofuranoside salt or a crystalline thionicotinamide-β-D-ribofuranoside salt, wherein the anion of the salt is a pharmaceutically acceptable anion such as chloride or any other pharmaceutically acceptable anion, starting from (a deprotected) product of formula Ia (O-Ia or S-Ia) or (a protected) product Va (O-Va or S-Va) as defined in the first aspect.

The target compounds may be prepared by at least three embodiments, i.e. either by exchanging the bromide ion in a compound of formula O-Ia or S-Ia via ion-exchange with a pharmaceutically acceptable anion such as chloride (embodiment 1); or deprotecting, i.e. cleaving the acyl groups in a compound of formula O-Va or S-Va in the presence of a pharmaceutically acceptable anion and protons such as hydrogen chloride, and subsequently subjecting the formed product to ion exchange with the respective pharmaceutically acceptable anion such as chloride (embodiment 2); or subjecting a compound of formula O-Va or S-Va to ion-exchange with a pharmaceutically acceptable anion such as chloride and subsequently deprotecting the formed ion-exchanged product with the respective acid of said pharmaceutically acceptable anion such as hydrogen chloride (embodiment 3).

These embodiments are discussed in the following in more detail.

Embodiment 1: Exchanging Bromide with Chloride or Another Pharmaceutically Acceptable Anion According to a specific embodiment, the invention relates to a method of making a crystalline nicotinamide-β-D-ribofuranoside chloride of formula O-Ib or a crystalline thionicotinamide-β-D-ribofuranoside chloride of formula S-Ib.

This method encompasses a method in which the product of formula O-Ia or S-Ia formed in the method according to the first aspect is subjected to ion exchange using an ion exchanger loaded with chloride ions.

Accordingly, in one embodiment, the invention comprises a method of making a crystalline nicotinamide-β-D-ribofuranoside chloride of formula O-Ib

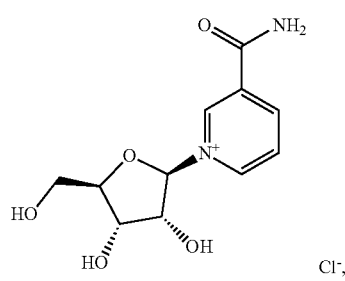

or a crystalline thionicotinamide-β-D-ribofuranoside chloride of formula S-Ib

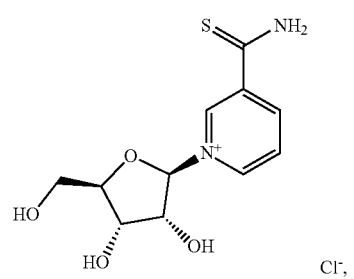

comprising step (b):
(b) subjecting the crystalline compound of formula O-Ia or S-Ia as defined in the first aspect [step (a)] to ion exchange using an ion exchanger loaded with chloride ions.

Suitable ion exchangers are known from the state of the art: The ion exchange may be performed by the commonly known methods.

The inventors further discovered that the method of converting the bromide of formula O-Ia or S-Ia to the chloride of formula O-Ib or S-Ib by ion exchange may be transferred to anions being different from chloride, but which may also be loaded to an ion-exchanger.

Basically, any anion may be used for ion exchange which is considered in the art as a pharmaceutically acceptable anion.

In a preferred embodiment, said anion is selected from an inorganic acid, preferably hydrogen sulfate, sulfate, dihydrogen phosphate, hydrogen phosphate, or phosphate.

Anions of organic acids may also be used. Suitable anions are preferably the anions of fumaric acid, maleic acid, succinic acid, citric acid, tartaric acid, acetic acid, and methane sulfonic acid.

Accordingly, the method according to the invention encompasses a method in which the product of formula O-Ia or S-Ia formed in the method according to the first aspect is subjected to ion exchange using an ion exchanger loaded with anions such as hydrogen sulfate or sulfate, preferably hydrogen sulfate, or dihydrogen phosphate, hydrogen phosphate, or phosphate, preferably dihydrogen phosphate, or fumaric acid, maleic acid, succinic acid, citric acid, tartaric acid, acetic acid and methane sulfonic acid.

Thus, in a further preferred embodiment, the invention relates to a method of making a crystalline (thio)nicotinamide-β-D-ribofuranoside salt, wherein the anion of the salt is a pharmaceutically acceptable anion, comprising step (bb):

(bb) subjecting the crystalline compound of formula O-Ia or S-Ia as defined in the first aspect to ion exchange using an ion exchanger loaded with a pharmaceutically acceptable anion.

The ion-exchange may be performed according to known methods. The exchange may be performed in water and/or organic solvents, depending on the solubility of the used starting material.

Embodiment 2: Deprotecting the Compound of Formula O-Va or S-Va in the Presence of Chloride or Another Pharmaceutically Acceptable Anion, Followed by Ion Exchange In another specific embodiment, at least a portion of the product formed in the cleavage according to step (D) as defined in the first aspect may be converted to the chloride, if the cleavage of the acyl groups, i.e. the deprotecting step, is performed in the presence of chloride ions.

In a preferred embodiment, the chloride ions stem from hydrogen chloride, i.e. cleavage is performed in the presence of hydrogen chloride, preferably hydrogen chloride in methanol. Then commonly a mixed salt is obtained, e.g. a mixture of bromide to chloride salt, e.g. in the range of from 20:80 to 30:70.

The mixed salt may then be subjected to an ion exchanger loaded with chloride ions in order to make the pure chloride of formula Ib.

However, depending on the load with chloride ions, mixtures of a bromide of formula Ia and chloride of formula Ib may be also prepared, if desired.

Likewise, it is also possible to convert at least a portion of the product formed in the cleavage according to step (D) as defined in the first aspect to a pharmaceutically acceptable anion different from chloride as disclosed above, if the cleavage is performed in the presence of said pharmaceutically acceptable anion.

In a preferred embodiment, the pharmaceutically acceptable anion stems from the respective acid, i.e. cleavage is performed in the presence of the respective acid, preferably the acid in methanol. Then usually a mixed salt is obtained, e.g. a mixture of bromide with the pharmaceutically acceptable anion.

The mixed salt may then be subjected to an ion exchanger loaded with the pharmaceutically acceptable anion in order to make the pure respective salt, if desired.

Thus, in a specific embodiment, the method comprises prior to step (b) step (c):

(c) deprotecting the compound of formula O-Va or S-Va obtained in step (B) or (C) as defined in the first aspect by removing the R groups, i.e. the acyl protecting groups, using hydrogen bromide in acetic acid in the presence of chloride ions.

In a more general embodiment, the method comprises prior to step (b) step (cc):

(cc) deprotecting the compound of formula Va (O-Va or S-Va) obtained in step (B) or (C) as defined in the first aspect by removing the R groups, i.e. the acyl protecting groups, using hydrogen bromide in acetic acid in the presence of a pharmaceutically acceptable anion.

Embodiment 3: Subjecting a Compound of Formula O-Va or S-Va to Ion Exchange with Chloride or Another Pharmaceutically Acceptable Anion, Followed by Deprotection In a further specific embodiment, it is also possible to exchange the bromide in a compound of formula O-Va or S-Va by chloride in an ion-exchanger loaded with chloride anions, and to subsequently deprotect the formed product O-Vb or S-Vb, i.e. to cleave the acyl groups from the riboside, when the formed product is subjected to hydrogen chloride.

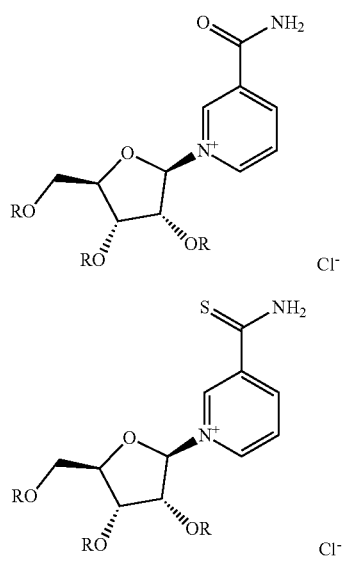

Accordingly, in a specific embodiment, the invention relates to a method of making a compound of formula O-Ib or S-Ib, comprising step (d):

(d) subjecting the crystalline compound of formula O-Va or S-Va as defined in the first aspect to ion exchange using an ion exchanger loaded with chloride ions.

Subsequently, the product obtained in step (d) is subjected to hydrochloric acid in order to deprotect the product formed in step (d), i.e. to cleave the acyl groups in order to obtain the target compound.

Accordingly, the method comprises step (e):

(e) subjecting the product formed in step (d) to hydrogen chloride.

In a more general embodiment, the crystalline compound of formula O-Va or S-Va as defined in the first aspect is subjected to ion exchange using an ion exchanger loaded with a pharmaceutically acceptable anion, and subsequently the product formed by ion exchange is subjected to the acid of the pharmaceutically acceptable anion, i.e. to the protonated pharmaceutically acceptable anion in order to deprotect the product formed in the ion exchange step, i.e. to cleave the acyl groups in order to obtain the target compound.

Thus, in a more general embodiment, the invention relates to a method of making a crystalline (thio)nicotinamide-β-D-ribofuranoside salt, wherein the anion of the salt is a pharmaceutically acceptable anion, comprising steps (d) and (e):

(d) subjecting the crystalline compound of formula O-Va or S-Va as defined in the first aspect to ion exchange using an ion exchanger loaded with a pharmaceutically acceptable anion;

(e) subjecting the product formed in step (d) to the protonated pharmaceutically acceptable anion.

It may be advantageous to perform the ion exchange according to embodiment 3, i.e. starting from (thio)nicotinamide-2,3,5-tri-O-acyl-β-D-riboside bromide of formula O-Va or of formula S-Va since compared to a compound of formula Va (thio)nicotinamide-β-D-ribofuranoside bromide of formula O-Ia or S-Ia commonly has a lower stability in water, respectively a worse solubility in organic solvents.

The salts such as (thio)nicotinamide-2,3,5-tri-O-acyl-β-D-ribofuranoside bromide of formula Va and target salts such as (thio)nicotinamide-β-D-ribofuranoside bromide of formula Ia and (thio)nicotinamide-β-D-ribofuranoside chloride of formula Ib made according to the methods of the invention are obtained in crystallized form. The amides are white to pale yellow solids, which are colorless in solution whereas the thioamides are bright yellow solids.

Crystallization may be evidenced by means of the respective powder X-ray diffraction patterns.

Crystalline (Thio)Nicotinamide-β-D-Ribofuranoside Salts (Third Aspect)

According to a third aspect, in one embodiment, the invention relates to a crystalline nicotinamide-2,3,5-tri-O-acetyl-β-D-ribofuranoside bromide of formula O-Va, wherein R=acetyl, characterized by a powder X-ray diffraction pattern as defined in FIG. 1.

The crystalline form may also be characterized by a powder X-ray diffraction pattern having peaks substantially as provided in Table 1, below, ±0.2 degrees two theta:

TABLE 1

| Pos. [°2Th.] | Height [cts] | FWHM Left [°2Th.] | d-spacing [Å] | Rel. Int. [%] |
|---|---|---|---|---|
| 4.8596 | 71292.27 | 0.0512 | 18.18452 | 100.00 |
| 9.7415 | 37099.07 | 0.0640 | 9.07962 | 52.04 |
| 11.0636 | 5303.51 | 0.0512 | 7.99743 | 7.44 |
| 11.6661 | 30006.17 | 0.0640 | 7.58568 | 42.09 |
| 12.5050 | 17088.05 | 0.0640 | 7.07866 | 23.97 |
| 14.1694 | 10910.62 | 0.0640 | 6.25069 | 15.30 |
| 14.3467 | 12561.22 | 0.0640 | 6.17384 | 17.62 |
| 14.6404 | 11886.06 | 0.0640 | 6.05064 | 16.67 |
| 15.0039 | 688.76 | 0.0768 | 5.90486 | 0.97 |
| 15.4402 | 22972.38 | 0.0640 | 5.73897 | 32.22 |
| 15.6066 | 12142.07 | 0.0768 | 5.67815 | 17.03 |
| 16.0891 | 7318.08 | 0.0768 | 5.50895 | 10.26 |
| 17.5371 | 5753.52 | 0.0640 | 5.05719 | 8.07 |
| 18.2959 | 29604.23 | 0.0768 | 4.84915 | 41.53 |
| 18.9874 | 4361.61 | 0.0512 | 4.67407 | 6.12 |
| 19.2100 | 20055.34 | 0.0640 | 4.62041 | 28.13 |

TABLE 1-continued

| Pos. [°2Th.] | Height [cts] | FWHM Left [°2Th.] | d-spacing [Å] | Rel. Int. [%] |
|---|---|---|---|---|
| 19.5686 | 65927.24 | 0.0895 | 4.53654 | 92.47 |
| 21.0763 | 6048.25 | 0.0640 | 4.21531 | 8.48 |
| 21.5928 | 24667.16 | 0.0512 | 4.11563 | 34.60 |
| 21.7919 | 68197.61 | 0.0768 | 4.07847 | 95.66 |
| 22.2517 | 51038.13 | 0.0640 | 3.99523 | 71.59 |
| 22.6057 | 16893.10 | 0.0640 | 3.93345 | 23.70 |
| 22.8833 | 3286.77 | 0.0640 | 3.88636 | 4.61 |
| 23.6485 | 9504.24 | 0.0512 | 3.76232 | 13.33 |
| 24.5338 | 1713.25 | 0.0640 | 3.62852 | 2.40 |
| 25.2389 | 6926.32 | 0.0640 | 3.52872 | 9.72 |
| 25.5511 | 2626.48 | 0.0512 | 3.48632 | 3.68 |
| 25.7810 | 10528.73 | 0.0512 | 3.45573 | 14.77 |
| 25.9964 | 46928.79 | 0.0768 | 3.42760 | 65.83 |
| 26.2806 | 27519.44 | 0.0640 | 3.39118 | 38.60 |
| 26.4612 | 15615.08 | 0.0512 | 3.36843 | 21.90 |
| 26.6836 | 9655.02 | 0.0640 | 3.34087 | 13.54 |
| 27.8914 | 10858.11 | 0.0640 | 3.19888 | 15.23 |
| 28.3122 | 16888.73 | 0.0768 | 3.15229 | 23.69 |
| 28.5824 | 10649.71 | 0.0640 | 3.12310 | 14.94 |
| 28.9526 | 2577.58 | 0.0640 | 3.08400 | 3.62 |
| 29.6768 | 7952.96 | 0.0768 | 3.01037 | 11.16 |
| 29.9687 | 5882.39 | 0.0780 | 2.97925 | 8.25 |
| 30.0860 | 4650.26 | 0.0768 | 2.97036 | 6.52 |
| 30.3809 | 9160.45 | 0.0640 | 2.94219 | 12.85 |
| 30.6233 | 5333.30 | 0.0512 | 2.91946 | 7.48 |
| 31.1502 | 5948.54 | 0.0768 | 2.87126 | 8.34 |
| 31.5383 | 983.58 | 0.0512 | 2.83681 | 1.38 |
| 31.7362 | 6573.29 | 0.0624 | 2.81724 | 9.22 |
| 31.8393 | 6262.96 | 0.0768 | 2.81067 | 8.78 |
| 32.3004 | 2514.90 | 0.0512 | 2.77160 | 3.53 |
| 32.5427 | 4936.80 | 0.0512 | 2.75151 | 6.92 |
| 32.7422 | 6711.15 | 0.0512 | 2.73520 | 9.41 |
| 33.5611 | 3857.26 | 0.0512 | 2.67031 | 5.41 |
| 34.0690 | 1950.96 | 0.0936 | 2.62948 | 2.74 |

Figure 2:
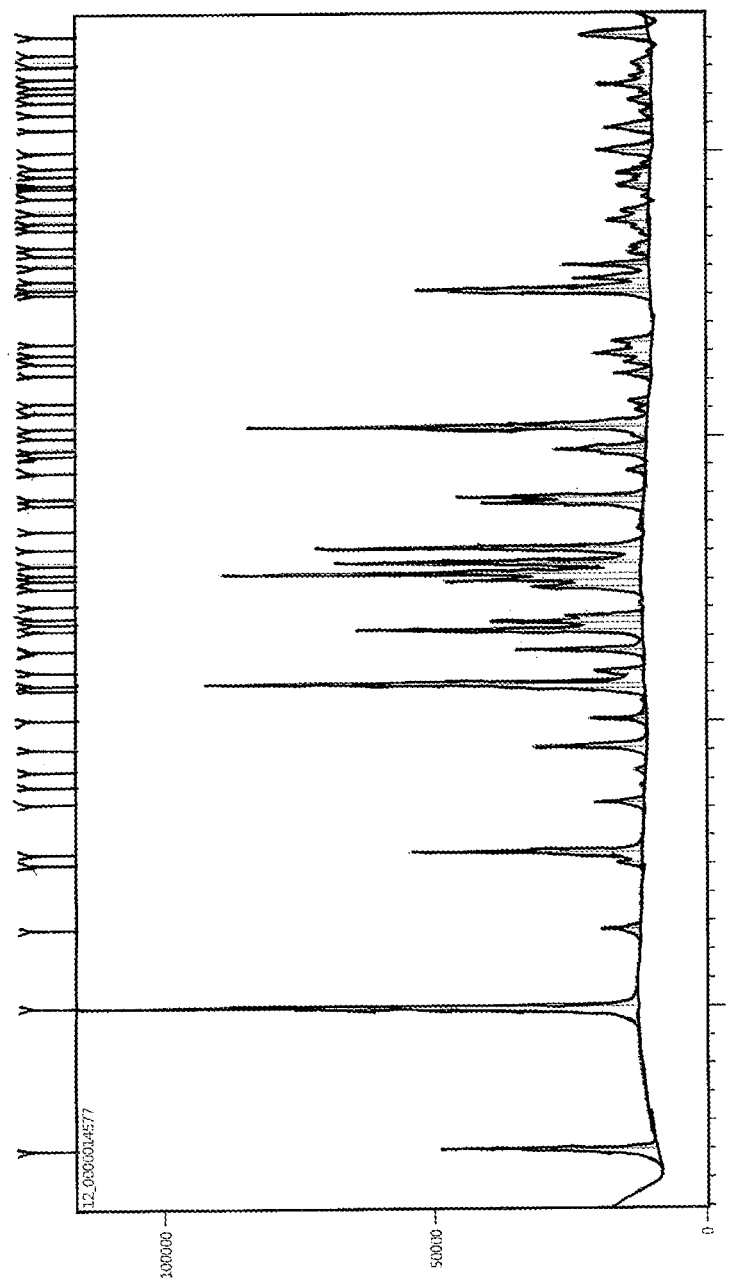
FIG. 2 shows a powder X-ray pattern of crystalline nicotinamide-β-D-ribofuranoside bromide of formula O-Ia.

In another embodiment, the invention relates to crystalline nicotinamide-β-D-ribofuranoside bromide of formula O-Ia characterized by a powder X-ray diffraction pattern as defined in FIG. 2.

The crystalline form may also be characterized by a powder X-ray diffraction pattern having peaks substantially as provided in Table 2, below, ±0.2 degrees two theta:

TABLE 2

| Pos. [°2Th.] | Height [cts] | FWHM Left [°2Th.] | d-spacing [Å] | Rel. Int. [%] |
|---|---|---|---|---|
| 4.9834 | 39915.85 | 0.0640 | 17.73310 | 38.04 |
| 9.9926 | 104925.60 | 0.0768 | 8.85207 | 100.00 |
| 12.7289 | 7488.57 | 0.0895 | 6.95464 | 7.14 |
| 15.0281 | 4745.79 | 0.0640 | 5.89541 | 4.52 |
| 15.4178 | 43099.99 | 0.0895 | 5.74727 | 41.08 |
| 17.1678 | 9579.68 | 0.0895 | 5.16515 | 9.13 |
| 17.7747 | 930.87 | 0.1023 | 4.99013 | 0.89 |
| 18.2972 | 2367.50 | 0.0895 | 4.84879 | 2.26 |
| 19.1099 | 21082.64 | 0.1151 | 4.64438 | 20.09 |
| 20.0800 | 10612.44 | 0.1023 | 4.42214 | 10.11 |
| 21.1406 | 19432.96 | 0.0512 | 4.20263 | 18.52 |
| 21.3367 | 81187.77 | 0.1023 | 4.16445 | 77.38 |
| 21.7779 | 9343.33 | 0.0895 | 4.08106 | 8.90 |
| 22.5050 | 23707.08 | 0.1023 | 3.95082 | 22.59 |
| 23.2212 | 63218.99 | 0.1023 | 3.83057 | 50.72 |
| 23.4862 | 27924.12 | 0.1023 | 3.78795 | 26.61 |
| 23.6753 | 14245.62 | 0.0768 | 3.75812 | 13.58 |
| 24.0921 | 550.38 | 0.1279 | 3.69403 | 0.52 |
| 24.7343 | 20396.95 | 0.1151 | 3.59955 | 19.44 |
| 24.9572 | 36507.45 | 0.0768 | 3.56791 | 34.79 |
| 25.1805 | 77901.20 | 0.1151 | 3.53677 | 74.24 |
| 25.5555 | 56498.90 | 0.1092 | 3.48284 | 53.86 |
| 25.6308 | 36562.21 | 0.0468 | 3.48141 | 34.85 |
| 26.0811 | 60634.70 | 0.1092 | 3.41383 | 57.79 |
| 26.7636 | 978.36 | 0.1560 | 3.32830 | 0.93 |
| 27.6511 | 30326.81 | 0.0780 | 3.22346 | 28.90 |

TABLE 2-continued

| Pos. [°2Th.] | Height [cts] | FWHM Left [°2Th.] | d-spacing [Å] | Rel. Int. [%] |
|---|---|---|---|---|
| 27.8528 | 34745.99 | 0.0936 | 3.20058 | 33.11 |
| 27.9323 | 17571.27 | 0.0468 | 3.19958 | 16.75 |
| 28.8151 | 3220.91 | 0.0936 | 3.09584 | 3.07 |
| 29.3715 | 8276.64 | 0.0780 | 3.03845 | 7.89 |
| 29.5362 | 17269.12 | 0.0780 | 3.02188 | 16.46 |
| 29.6387 | 10238.93 | 0.0624 | 3.01914 | 9.76 |
| 29.9900 | 2526.55 | 0.0936 | 2.97718 | 2.41 |
| 30.3279 | 73767.23 | 0.0936 | 2.94477 | 70.30 |
| 30.4006 | 45680.79 | 0.0468 | 2.94520 | 43.54 |
| 30.8843 | 2342.44 | 0.0936 | 2.89297 | 2.23 |
| 31.2148 | 3499.82 | 0.0936 | 2.86309 | 3.34 |
| 32.2063 | 6972.10 | 0.0624 | 2.77718 | 6.64 |
| 32.6193 | 4935.69 | 0.0780 | 2.74296 | 4.70 |
| 32.8912 | 10921.30 | 0.0780 | 2.72090 | 10.41 |
| 33.3108 | 7332.05 | 0.0936 | 2.68757 | 6.99 |
| 35.0536 | 35425.14 | 0.0780 | 2.55784 | 33.76 |
| 35.1640 | 43507.22 | 0.0780 | 2.55007 | 41.46 |
| 35.2887 | 16436.92 | 0.0468 | 2.54765 | 15.67 |
| 35.5397 | 13765.55 | 0.0780 | 2.52396 | 13.12 |
| 36.0064 | 16502.96 | 0.0936 | 2.49231 | 15.73 |
| 36.1080 | 7558.48 | 0.0468 | 2.49171 | 7.20 |
| 36.4748 | 4177.84 | 0.0936 | 2.46137 | 3.98 |
| 36.7106 | 3655.13 | 0.0780 | 2.44610 | 3.48 |
| 37.3013 | 3317.08 | 0.0624 | 2.40872 | 3.16 |

Figure 3:
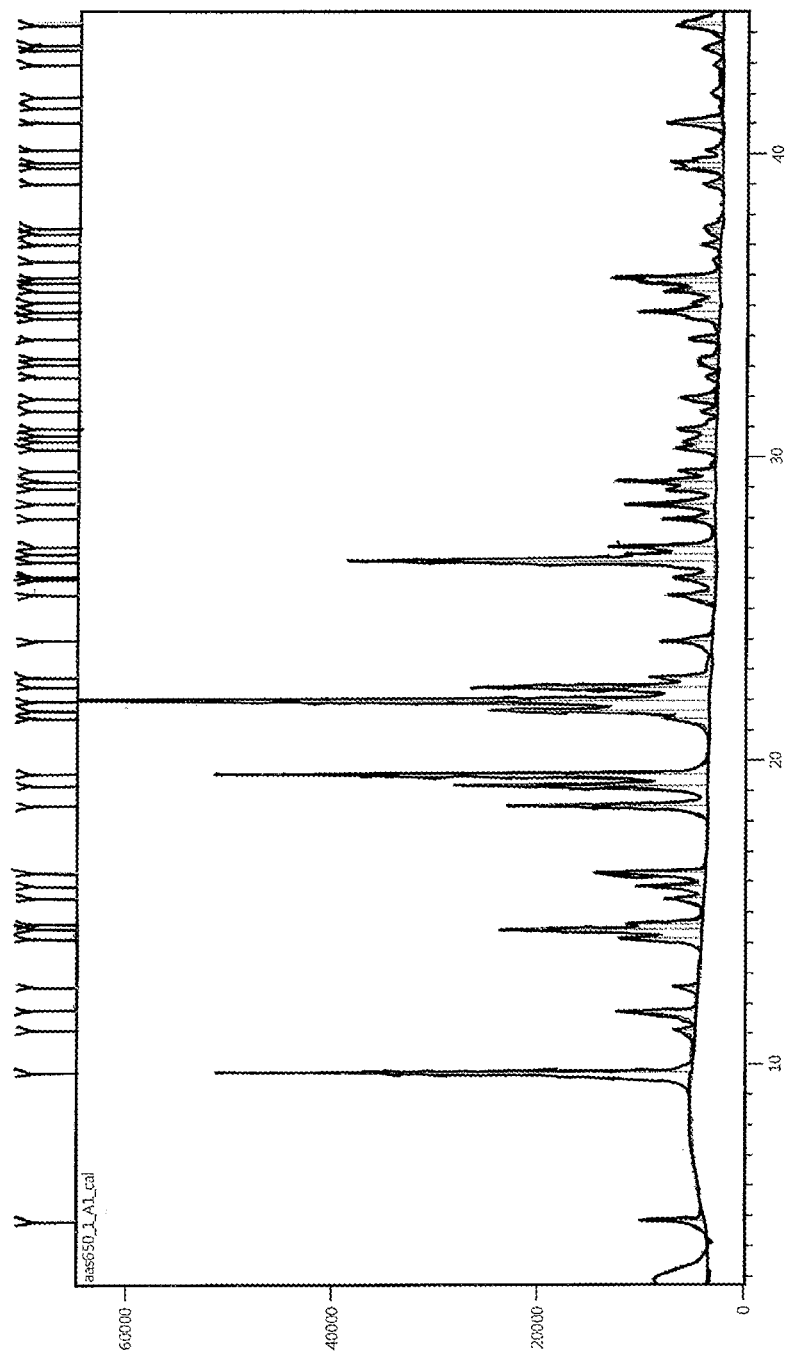
FIG. 3 shows a powder X-ray pattern of crystalline nicotinamide-2,3,5-tri-O-acetyl-β-D-ribofuranoside chloride of formula O-Vb (R=acetyl)

In another embodiment, the invention relates to a crystalline nicotinamide-2,3,5-tri-O-acetyl-β-D-ribofuranoside chloride of formula O-Vb characterized by a powder X-ray diffraction pattern as defined in FIG. 3.

The crystalline form may also be characterized by a powder X-ray diffraction pattern having peaks substantially as provided in Table 3, below, ±0.2 degrees two theta:

TABLE 3

| Pos. [°2Th.] | Height [cts] | FWHM Left [°2Th.] | d-spacing [Å] | Rel. Int. [%] |
|---|---|---|---|---|
| 4.8475 | 6417.96 | 0.0512 | 18.22981 | 10.38 |
| 9.7319 | 46396.97 | 0.0768 | 9.08855 | 75.06 |
| 11.1326 | 2222.54 | 0.0895 | 7.94800 | 3.60 |
| 11.7525 | 7751.80 | 0.1151 | 7.53014 | 12.54 |
| 12.5411 | 2693.25 | 0.1023 | 7.05833 | 4.36 |
| 14.1524 | 8155.33 | 0.1151 | 6.25815 | 13.19 |
| 14.4494 | 19748.00 | 0.1279 | 6.13020 | 31.95 |
| 14.6138 | 7305.56 | 0.0640 | 6.06157 | 11.82 |
| 15.4504 | 3780.59 | 0.0768 | 5.73520 | 6.12 |
| 15.8654 | 6665.39 | 0.1151 | 5.58609 | 10.78 |
| 16.3133 | 11068.90 | 0.1151 | 5.43308 | 17.91 |
| 18.5224 | 19458.24 | 0.1279 | 4.79034 | 31.48 |
| 19.1777 | 24721.89 | 0.1279 | 4.62812 | 40.00 |
| 19.5514 | 47962.12 | 0.1023 | 4.54049 | 77.60 |
| 21.3779 | 4494.25 | 0.0768 | 4.15651 | 7.27 |
| 21.6771 | 21463.64 | 0.0895 | 4.09981 | 34.72 |
| 21.9841 | 61810.63 | 0.1151 | 4.04325 | 100.00 |
| 22.4229 | 23441.39 | 0.1023 | 3.96511 | 37.92 |
| 22.7501 | 5967.33 | 0.0895 | 3.90881 | 9.65 |
| 23.9418 | 5090.24 | 0.1151 | 3.71689 | 8.24 |
| 25.4363 | 4660.75 | 0.1023 | 3.50179 | 7.54 |
| 25.9756 | 4050.70 | 0.0780 | 3.42745 | 6.55 |
| 26.0480 | 3956.44 | 0.0512 | 3.42093 | 6.40 |
| 26.5839 | 35761.91 | 0.1407 | 3.35317 | 57.86 |
| 26.7937 | 8733.41 | 0.0512 | 3.32739 | 14.13 |
| 27.0585 | 10338.22 | 0.1023 | 3.29642 | 16.73 |
| 27.9629 | 5175.38 | 0.1279 | 3.19086 | 8.37 |
| 28.4388 | 8827.46 | 0.1279 | 3.13854 | 14.28 |
| 28.9342 | 4867.77 | 0.1023 | 3.08592 | 7.88 |
| 29.1871 | 9899.74 | 0.1151 | 3.05976 | 16.02 |
| 29.5207 | 3827.12 | 0.1023 | 3.02594 | 6.19 |
| 30.2684 | 4111.40 | 0.1023 | 2.95287 | 6.65 |
| 30.4970 | 3424.80 | 0.0768 | 2.93125 | 5.54 |
| 30.6819 | 2181.97 | 0.0512 | 2.91401 | 3.53 |
| 30.9229 | 3888.20 | 0.0895 | 2.89185 | 6.29 |
| 31.5061 | 1895.93 | 0.0895 | 2.83963 | 3.07 |

TABLE 3-continued

| Pos. [°2Th.] | Height [cts] | FWHM Left [°2Th.] | d-spacing [Å] | Rel. Int. [%] |
|---|---|---|---|---|
| 31.9376 | 3794.97 | 0.0895 | 2.80225 | 6.14 |
| 32.6368 | 1221.55 | 0.1535 | 2.74379 | 1.98 |
| 33.0340 | 2110.89 | 0.0768 | 2.71170 | 3.42 |
| 33.2355 | 2214.18 | 0.0640 | 2.69572 | 3.58 |
| 33.8728 | 2956.74 | 0.0768 | 2.64645 | 4.78 |
| 34.5515 | 2843.73 | 0.1023 | 2.59600 | 4.60 |
| 34.7925 | 7970.30 | 0.0768 | 2.57857 | 12.89 |
| 35.0864 | 2845.65 | 0.0895 | 2.55764 | 4.60 |
| 35.4559 | 5572.16 | 0.0895 | 2.53183 | 9.01 |
| 35.7436 | 8015.40 | 0.0780 | 2.51003 | 12.97 |
| 35.9103 | 10571.39 | 0.1151 | 2.50083 | 17.10 |
| 36.4863 | 901.07 | 0.1023 | 2.46266 | 1.46 |
| 37.0231 | 2078.04 | 0.0895 | 2.42818 | 3.36 |
| 37.3756 | 1277.41 | 0.0768 | 2.40609 | 2.07 |

Figure 4:
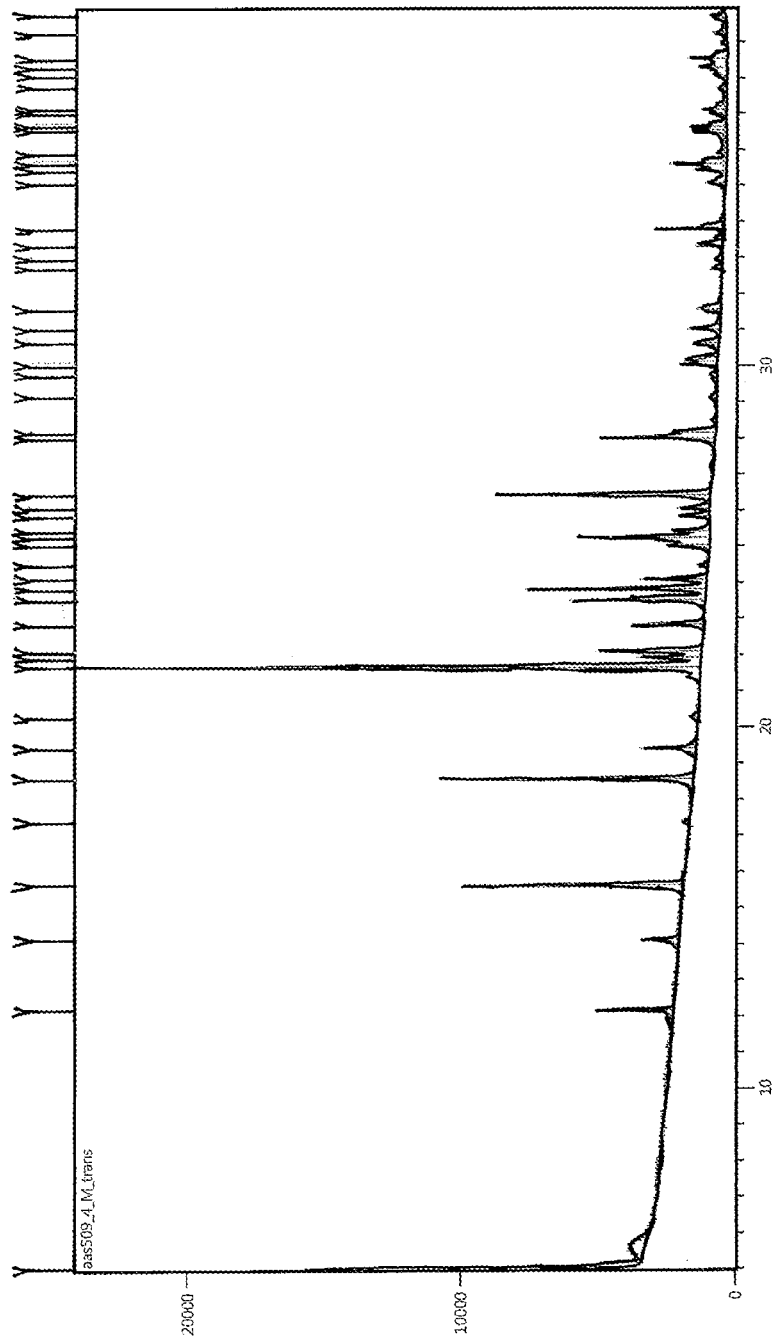
FIG. 4 shows a powder X-ray pattern of crystalline nicotinamide-β-D-ribofuranoside chloride of formula O-Ib.

In another embodiment, the invention relates to a crystalline nicotinamide-β-D-ribofuranoside chloride of formula O-Ib characterized by a powder X-ray diffraction pattern as defined in FIG. 4.

The crystalline form may also be characterized by a powder X-ray diffraction pattern having peaks substantially as provided in Table 4, below, ±0.2 degrees two theta:

TABLE 4

| Pos. [°2Th.] | Height [cts] | FWHM Left [°2Th.] | d-spacing [Å] | Rel. Int. [%] |
|---|---|---|---|---|
| 5.0231 | 8989.67 | 0.0384 | 17.59305 | 39.07 |
| 12.1684 | 2813.03 | 0.0512 | 7.27371 | 12.22 |
| 14.1132 | 1403.11 | 0.0640 | 6.27546 | 6.10 |
| 15.6279 | 8040.27 | 0.0512 | 5.67047 | 34.94 |
| 17.3905 | 290.12 | 0.0768 | 5.09950 | 1.26 |
| 18.5579 | 9325.15 | 0.0768 | 4.78127 | 40.52 |
| 19.4055 | 2040.30 | 0.0640 | 4.57430 | 8.87 |
| 20.2755 | 328.10 | 0.0768 | 4.37994 | 1.43 |
| 21.6623 | 23012.07 | 0.0768 | 4.10258 | 100.00 |
| 21.9250 | 2287.87 | 0.0512 | 4.05402 | 9.94 |
| 22.1043 | 3821.40 | 0.0512 | 4.02153 | 16.61 |
| 22.8310 | 2687.12 | 0.0640 | 3.89514 | 11.68 |
| 23.5039 | 4901.46 | 0.0512 | 3.78513 | 21.30 |
| 23.8061 | 6551.87 | 0.0512 | 3.73777 | 28.47 |
| 24.0791 | 2424.61 | 0.0512 | 3.69600 | 10.54 |
| 24.4847 | 304.96 | 0.0768 | 3.63569 | 1.33 |
| 25.0212 | 1591.60 | 0.0512 | 3.55893 | 6.92 |
| 25.2426 | 4900.73 | 0.0384 | 3.52822 | 21.30 |
| 25.4137 | 1375.46 | 0.0384 | 3.50484 | 5.98 |
| 25.8290 | 1207.51 | 0.0384 | 3.44943 | 5.25 |
| 26.0464 | 1224.32 | 0.0512 | 3.42113 | 5.32 |
| 26.4267 | 7816.55 | 0.0512 | 3.37276 | 33.97 |
| 28.0059 | 4178.39 | 0.0384 | 3.18607 | 18.16 |
| 28.1526 | 1630.03 | 0.0384 | 3.16980 | 7.08 |
| 29.1551 | 207.40 | 0.1023 | 3.06304 | 0.90 |
| 29.7413 | 197.40 | 0.0768 | 3.00399 | 0.86 |
| 30.0261 | 1277.41 | 0.0624 | 2.97368 | 5.55 |
| 30.1291 | 1167.49 | 0.0468 | 2.97111 | 5.07 |
| 30.6207 | 899.57 | 0.0624 | 2.91727 | 3.91 |
| 31.0112 | 1136.20 | 0.0624 | 2.88142 | 4.94 |
| 31.5753 | 873.21 | 0.0624 | 2.83122 | 3.79 |
| 32.6926 | 413.90 | 0.0624 | 2.73697 | 1.80 |
| 32.9720 | 120.06 | 0.1248 | 2.71441 | 0.52 |
| 33.3259 | 934.40 | 0.0624 | 2.68639 | 4.06 |
| 33.7902 | 2305.04 | 0.0468 | 2.65053 | 10.02 |
| 35.0795 | 663.05 | 0.0624 | 2.55601 | 2.88 |
| 35.4164 | 1125.19 | 0.0780 | 2.53247 | 4.89 |
| 35.5939 | 1969.88 | 0.0468 | 2.52025 | 8.56 |
| 35.6948 | 731.01 | 0.0468 | 2.51959 | 3.18 |
| 35.8891 | 190.71 | 0.0936 | 2.50019 | 0.83 |
| 36.5120 | 1149.56 | 0.0624 | 2.45889 | 5.00 |
| 36.6270 | 1264.06 | 0.0624 | 2.45149 | 5.49 |
| 36.7356 | 505.49 | 0.0468 | 2.45057 | 2.20 |
| 36.9895 | 579.35 | 0.0468 | 2.42830 | 2.52 |
| 37.0895 | 896.19 | 0.0468 | 2.42198 | 3.89 |
| 37.7257 | 287.11 | 0.0624 | 2.38258 | 1.25 |

TABLE 4-continued

| Pos. [°2Th.] | Height [cts] | FWHM Left [°2Th.] | d-spacing [Å] | Rel. Int. [%] |
|---|---|---|---|---|
| 38.0622 | 290.59 | 0.0624 | 2.36229 | 1.26 |
| 38.2889 | 929.40 | 0.0624 | 2.34883 | 4.04 |
| 38.5465 | 1392.21 | 0.0624 | 2.33372 | 6.05 |
| 39.2478 | 426.81 | 0.0468 | 2.29362 | 1.85 |

Figure 5:
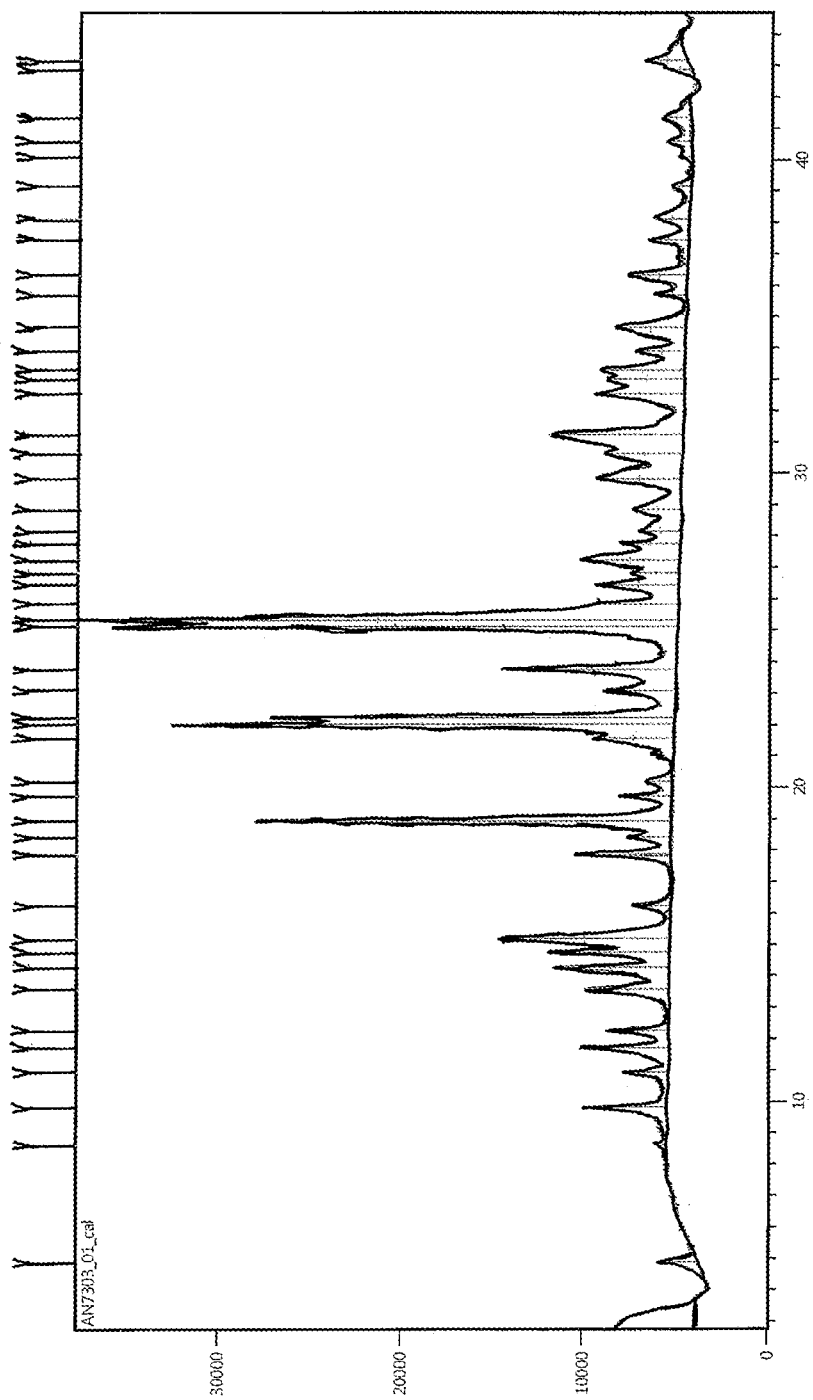
FIG. 5 shows a powder X-ray pattern of crystalline thionicotinamide-2,3,5-tri-O-acetyl-β-D-ribofuranoside bromide of formula S-Va (R=acetyl)

In another embodiment, the invention relates to a crystalline thionicotinamide-2,3,5-tri-O-acetyl-β-D-ribofuranoside bromide of formula S-Va characterized by a powder X-ray diffraction pattern as defined in FIG. 5.

The crystalline form may also be characterized by a powder X-ray diffraction pattern having peaks substantially as provided in Table 5, below, ±0.2 degrees two theta:

TABLE 5

| Pos. [°2Th.] | Height [cts] | FWHM Left [°2Th.] | d-spacing [Å] | Rel. Int. [%] |
|---|---|---|---|---|
| 4.8788 | 2195.81 | 0.1151 | 18.11281 | 6.67 |
| 8.6324 | 562.38 | 0.1535 | 10.24356 | 1.71 |
| 9.8052 | 4588.76 | 0.1407 | 9.02084 | 13.94 |
| 10.9161 | 2430.77 | 0.0895 | 8.10515 | 7.39 |
| 11.7011 | 4745.31 | 0.1151 | 7.56313 | 14.42 |
| 12.2585 | 3471.50 | 0.1407 | 7.22043 | 10.55 |
| 13.6772 | 4531.78 | 0.1279 | 6.52196 | 13.77 |
| 14.2573 | 6393.38 | 0.1279 | 6.21235 | 19.42 |
| 14.7500 | 6406.26 | 0.1151 | 6.00592 | 19.46 |
| 15.1647 | 9320.06 | 0.2047 | 5.84259 | 28.32 |
| 16.2418 | 2032.69 | 0.1635 | 5.45748 | 0.18 |
| 17.8283 | 4849.34 | 0.0624 | 4.97113 | 14.73 |
| 17.8768 | 5300.32 | 0.0768 | 4.96186 | 16.10 |
| 18.4082 | 2433.54 | 0.1535 | 4.81981 | 7.39 |
| 18.9466 | 22896.43 | 0.1535 | 4.68405 | 69.56 |
| 19.7172 | 2877.50 | 0.1279 | 4.50268 | 8.74 |
| 20.1743 | 1526.96 | 0.2303 | 4.40168 | 4.64 |
| 21.5591 | 4533.93 | 0.0895 | 4.12198 | 13.78 |
| 22.0089 | 27593.16 | 0.1279 | 4.03875 | 83.83 |
| 22.2230 | 22178.52 | 0.1279 | 4.00031 | 67.38 |
| 23.0797 | 3922.13 | 0.1151 | 3.85373 | 11.92 |
| 23.7722 | 9540.90 | 0.1407 | 3.74301 | 28.99 |
| 25.1244 | 30816.66 | 0.1279 | 3.54455 | 93.63 |
| 25.3299 | 32913.99 | 0.1407 | 3.51626 | 100.00 |
| 25.8477 | 4209.14 | 0.1279 | 3.44680 | 12.79 |
| 26.4377 | 4383.83 | 0.2047 | 3.37138 | 13.32 |
| 26.8112 | 2621.74 | 0.153.5 | 3.32525 | 7.97 |
| 27.2214 | 5428.42 | 0.1407 | 3.27607 | 16.49 |
| 27.7450 | 3180.25 | 0.1279 | 3.21542 | 9.66 |
| 28.1516 | 2220.15 | 0.1279 | 3.16990 | 6.75 |
| 28.8400 | 2548.30 | 0.1279 | 3.09579 | 7.74 |
| 29.8370 | 4742.47 | 0.1663 | 2.99467 | 14.41 |
| 30.6274 | 4206.50 | 0.1279 | 2.91907 | 12.78 |
| 31.2475 | 6977.86 | 0.1023 | 2.86254 | 21.20 |
| 32.5230 | 4890.17 | 0.1151 | 2.75313 | 14.86 |
| 33.0231 | 4118.05 | 0.2047 | 2.71257 | 12.51 |
| 33.2980 | 4648.12 | 0.1407 | 2.69081 | 14.12 |
| 33.9066 | 2645.51 | 0.2558 | 2.64389 | 8.04 |
| 34.6497 | 3868.41 | 0.2558 | 2.58887 | 11.75 |
| 35.6984 | 1714.59 | 0.1535 | 2.51519 | 5.21 |
| 36.3222 | 3218.75 | 0.2303 | 2.47341 | 9.78 |
| 37.4379 | 2218.49 | 0.2047 | 2.40223 | 6.74 |
| 38.1309 | 1821.27 | 0.1791 | 2.36015 | 5.53 |
| 39.4474 | 927.52 | 0.2047 | 2.30117 | 2.82 |
| 40.0903 | 720.91 | 0.1023 | 2.24920 | 2.19 |
| 40.5865 | 1295.24 | 0.1023 | 2.22284 | 3.94 |
| 41.3424 | 1422.63 | 0.1535 | 2.18393 | 4.32 |
| 42.8690 | 1208.13 | 0.1535 | 2.10963 | 3.6 |
| 43.1670 | 2207.61 | 0.1535 | 2.09575 | 6.71 |

Figure 6:
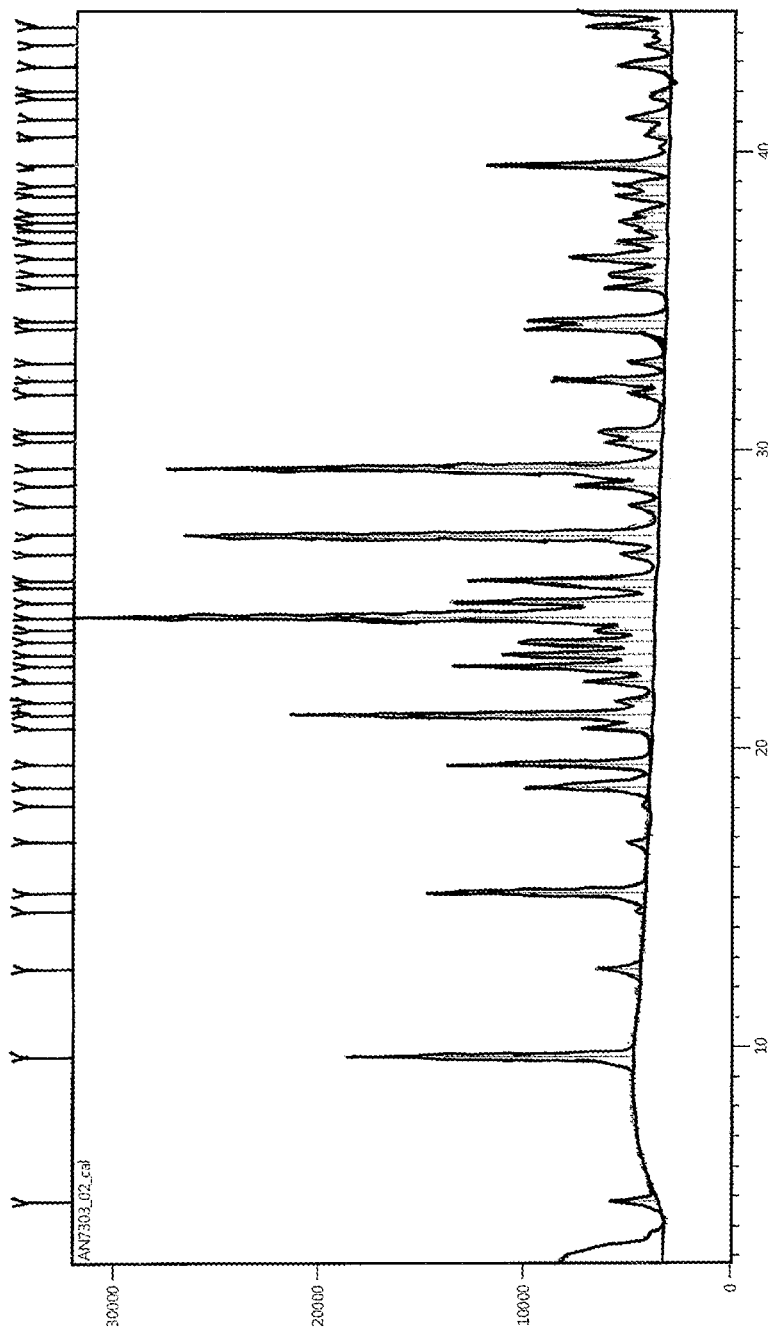
FIG. 6 shows a powder X-ray pattern of crystalline thionicotinamide-β-D-ribofuranoside bromide of formula S-Ia.

In another embodiment, the invention relates to a crystalline thionicotinamide-β-D-ribofuranoside bromide of formula S-Ia characterized by a powder X-ray diffraction pattern as defined in FIG. 6.

The crystalline form may also be characterized by a powder X-ray diffraction pattern having peaks substantially as provided in Table 6, below, ±0.2 degrees two theta:

TABLE 6

| Pos. [°2Th.] | Height [cts] | FWHM Left [°2Th.] | d-spacing [Å] | Rel. Int. [%] |
|---|---|---|---|---|
| 4.8263 | 2278.31 | 0.0768 | 18.30980 | 8.03 |
| 9.6801 | 14078.37 | 0.0895 | 9.13713 | 49.60 |
| 12.6028 | 2173.34 | 0.1279 | 7.02393 | 7.66 |
| 14.5631 | 352.02 | 0.1535 | 6.08257 | 1.24 |
| 15.1699 | 10647.52 | 0.1279 | 5.84062 | 37.51 |
| 16.8482 | 982.08 | 0.1535 | 5.26240 | 3.46 |
| 18.0591 | 257.63 | 0.2047 | 4.91219 | 0.91 |
| 18.6922 | 6117.69 | 0.1151 | 4.74722 | 21.55 |
| 19.4549 | 9894.90 | 0.1023 | 4.56280 | 34.86 |
| 20.6633 | 3359.40 | 0.1279 | 4.29860 | 11.84 |
| 21.1290 | 17624.66 | 0.1791 | 4.20490 | 62.09 |
| 21.5537 | 1681.31 | 0.1023 | 4.12301 | 5.92 |
| 22.2306 | 3338.13 | 0.1407 | 3.99897 | 11.76 |
| 22.7431 | 9818.91 | 0.1663 | 3.91001 | 34.59 |
| 23.1593 | 7370.57 | 0.1407 | 3.84066 | 25.97 |
| 23.5649 | 6627.76 | 0.1407 | 3.77547 | 23.35 |
| 23.9657 | 2892.60 | 0.1407 | 3.71323 | 10.19 |
| 24.3932 | 28384.03 | 0.1791 | 3.64912 | 100.00 |
| 24.8879 | 9967.23 | 0.1279 | 3.57770 | 35.12 |
| 25.3853 | 3199.46 | 0.1023 | 3.50871 | 11.27 |
| 25.6331 | 9149.39 | 0.1407 | 3.47534 | 32.23 |
| 26.4737 | 1905.94 | 0.1279 | 3.36688 | 6.71 |
| 27.1198 | 23107.26 | 0.1791 | 3.28811 | 81.41 |
| 28.1027 | 1337.27 | 0.1279 | 3.17531 | 4.71 |
| 28.7725 | 4230.01 | 0.1407 | 3.10289 | 14.90 |
| 29.3727 | 24117.60 | 0.1248 | 3.03832 | 84.97 |
| 29.4398 | 20316.94 | 0.0634 | 3.03908 | 71.58 |
| 30.2656 | 2777.86 | 0.0936 | 2.95069 | 9.79 |
| 30.5945 | 2989.91 | 0.1248 | 2.91971 | 10.53 |
| 31.8537 | 1694.75 | 0.1092 | 2.80711 | 5.97 |
| 32.3235 | 5502.72 | 0.1716 | 2.76737 | 19.39 |
| 32.9021 | 1649.42 | 0.1872 | 2.72002 | 5.81 |
| 34.0540 | 6762.12 | 0.1248 | 2.63060 | 23.82 |
| 34.3285 | 6745.81 | 0.1248 | 2.61020 | 23.77 |
| 35.4687 | 2867.35 | 0.2340 | 2.52885 | 10.10 |
| 35.9066 | 2636.15 | 0.3120 | 2.49901 | 9.29 |
| 36.4103 | 4708.75 | 0.1716 | 2.46558 | 16.59 |
| 36.9346 | 2540.82 | 0.1248 | 2.43178 | 8.95 |
| 37.3399 | 1585.95 | 0.1872 | 2.40631 | 5.59 |
| 37.6298 | 2307.02 | 0.1560 | 2.38844 | 8.13 |
| 37.9333 | 1564.59 | 0.2184 | 2.37002 | 5.51 |
| 38.5213 | 2557.83 | 0.1092 | 2.33519 | 9.01 |
| 38.8557 | 2678.86 | 0.1248 | 2.31586 | 9.44 |
| 39.5049 | 8914.12 | 0.1092 | 2.27928 | 31.41 |
| 39.5830 | 8086.04 | 0.0780 | 2.28061 | 28.49 |
| 40.5200 | 1109.47 | 0.1404 | 2.22249 | 3.91 |
| 41.1098 | 2048.76 | 0.2184 | 2.19393 | 7.22 |
| 41.7700 | 1066.47 | 0.1560 | 2.16077 | 3.76 |
| 41.9990 | 779.91 | 0.1872 | 2.14951 | 2.75 |
| 42.8567 | 2660.17 | 0.1248 | 2.10846 | 9.37 |

Figure 7:
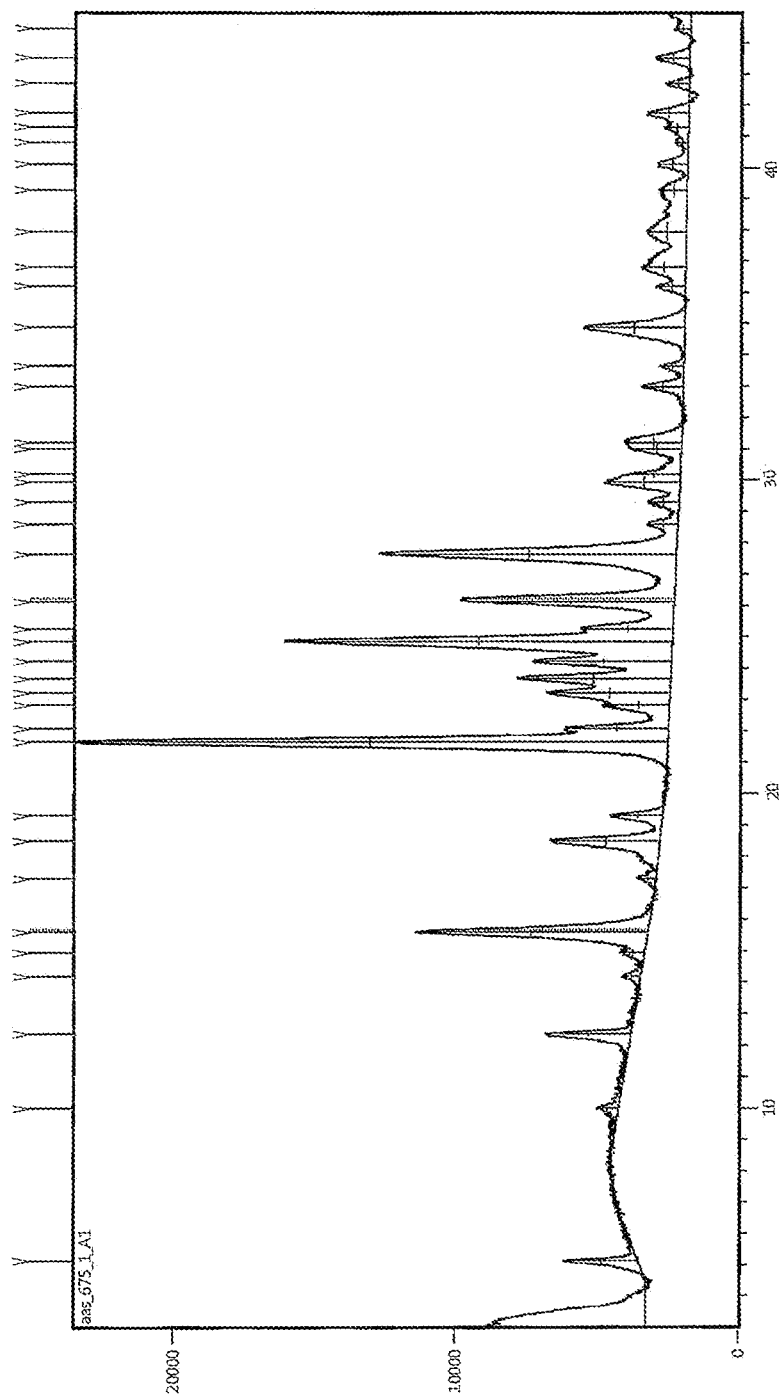
FIG. 7 shows a powder X-ray pattern of crystalline thionicotinamide-β-D-ribofuranoside chloride of formula S-Ib.

In another embodiment, the invention relates to crystalline thionicotinamide-β-D-ribofuranoside chloride of formula S-Ib characterized by a powder X-ray diffraction pattern as defined in FIG. 7.

The crystalline form may also be characterized by a powder X-ray diffraction pattern having peaks substantially as provided in Table 7, below, ±0.2 degrees two theta:

TABLE 7

| Pos. [°2Th.] | Height [cts] | FWHM Left [°2Th.] | d-spacing [Å] | Rel. Int. [%] |
|---|---|---|---|---|
| 5.1072 | 2596.08 | 0.1407 | 17.30350 | 12.31 |
| 9.9887 | 750.86 | 0.1535 | 8.85552 | 3.56 |
| 12.3314 | 2986.69 | 0.0895 | 7.17791 | 14.17 |
| 14.1590 | 596.22 | 0.2047 | 6.25523 | 2.83 |
| 14.9235 | 770.31 | 0.1535 | 5.93649 | 3.65 |
| 15.5744 | 8180.18 | 0.1716 | 5.68511 | 38.80 |
| 15.6423 | 7419.05 | 0.0780 | 5.67464 | 35.19 |
| 17.2676 | 554.86 | 0.2496 | 5.13128 | 2.63 |
| 18.4501 | 3815.59 | 0.2496 | 4.80498 | 18.10 |
| 19.2735 | 1749.74 | 0.1248 | 4.60152 | 8.30 |
| 21.6073 | 21083.66 | 0.3276 | 4.10949 | 100.00 |
| 22.0435 | 3617.26 | 0.1248 | 4.02915 | 17.16 |
| 22.7953 | 2232.49 | 0.2184 | 3.89794 | 10.59 |
| 23.1851 | 4285.33 | 0.2496 | 3.83327 | 20.33 |
| 23.6470 | 5385.96 | 0.2340 | 3.75944 | 25.55 |
| 24.2027 | 4758.83 | 0.1248 | 3.67437 | 22.57 |
| 24.8374 | 13692.29 | 0.2496 | 3.58189 | 64.94 |
| 25.2280 | 3183.22 | 0.1560 | 3.52731 | 15.10 |
| 26.0958 | 7252.40 | 0.1248 | 3.41195 | 34.40 |
| 26.1900 | 7230.56 | 0.0780 | 3.40834 | 34.29 |
| 27.6167 | 10363.59 | 0.2496 | 3.22740 | 49.15 |
| 28.5770 | 1049.57 | 0.2808 | 3.12109 | 4.98 |
| 29.2742 | 1090.63 | 0.3120 | 3.04833 | 5.17 |
| 29.8993 | 2582.37 | 0.3120 | 2.98600 | 12.25 |
| 30.1497 | 1826.12 | 0.1872 | 2.96177 | 8.66 |
| 30.9751 | 1763.02 | 0.2496 | 2.88470 | 8.36 |
| 31.1711 | 1963.57 | 0.3432 | 2.86701 | 9.31 |
| 32.9684 | 1435.80 | 0.3120 | 2.71470 | 6.81 |
| 33.6199 | 770.78 | 0.1872 | 2.66357 | 3.66 |
| 34.8531 | 3520.86 | 0.3744 | 2.57210 | 16.70 |
| 36.1670 | 972.10 | 0.2496 | 2.48162 | 4.61 |
| 36.7771 | 1506.66 | 0.2808 | 2.44183 | 7.15 |
| 37.9104 | 1370.92 | 0.5616 | 2.37140 | 6.50 |
| 39.2448 | 901.73 | 0.3744 | 2.29378 | 4.28 |
| 40.0799 | 1048.09 | 0.2808 | 2.24790 | 4.97 |
| 40.8062 | 428.39 | 0.1872 | 2.20955 | 2.03 |
| 41.2829 | 782.56 | 0.1872 | 2.18513 | 3.71 |
| 41.7217 | 1452.32 | 0.3120 | 2.16315 | 6.89 |
| 42.6907 | 809.28 | 0.3120 | 2.11627 | 3.84 |
| 43.5291 | 1167.24 | 0.3744 | 2.07744 | 5.54 |
| 44.4617 | 535.56 | 0.2184 | 2.03600 | 2.54 |

Figure 8:
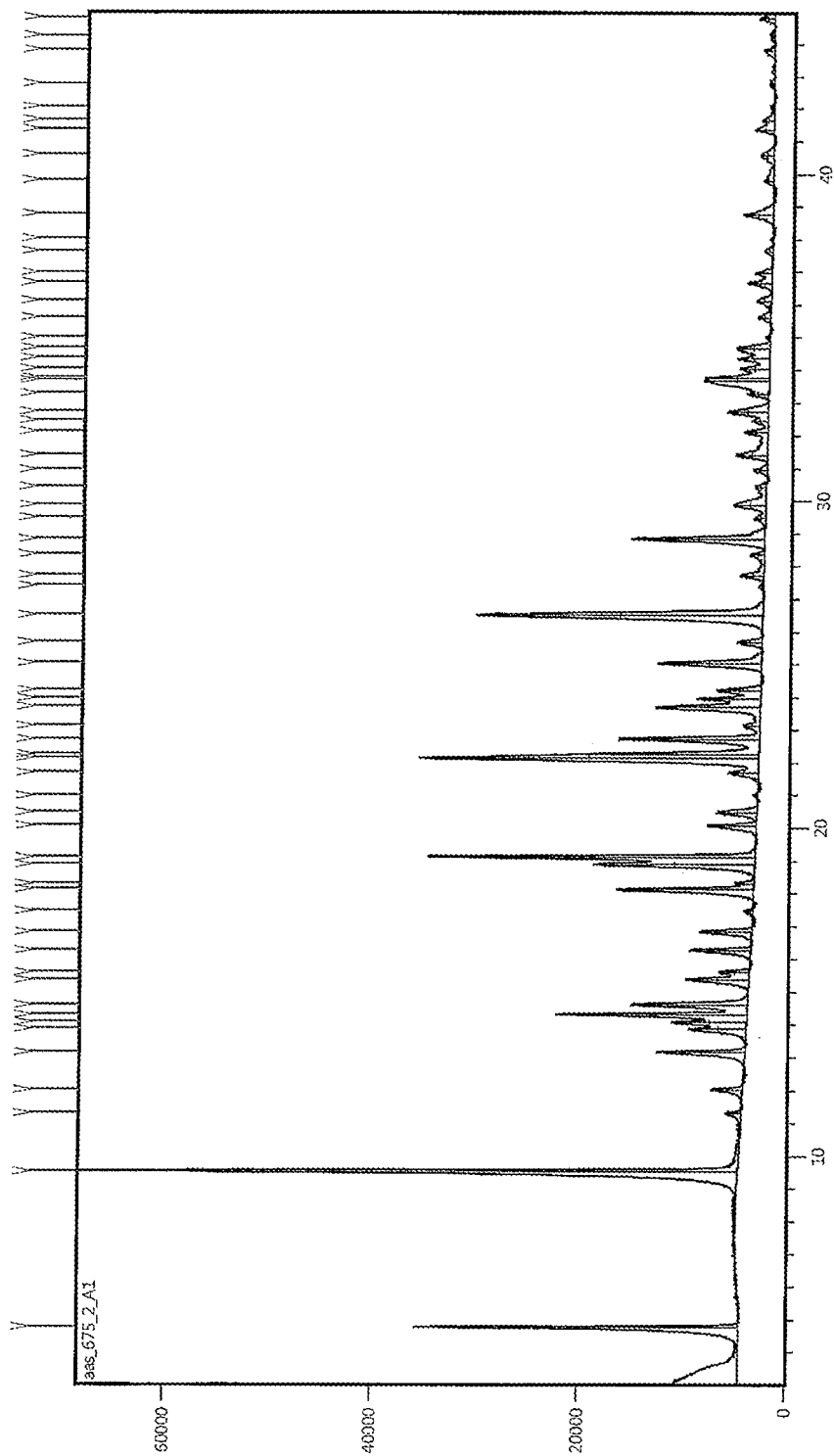
FIG. 8 shows a powder X-ray pattern of crystalline thionicotinamide-2,3,5-tri-O-acetyl β-D-ribofuranoside chloride of formula S-Vb (R=acetyl)
Figure 9:
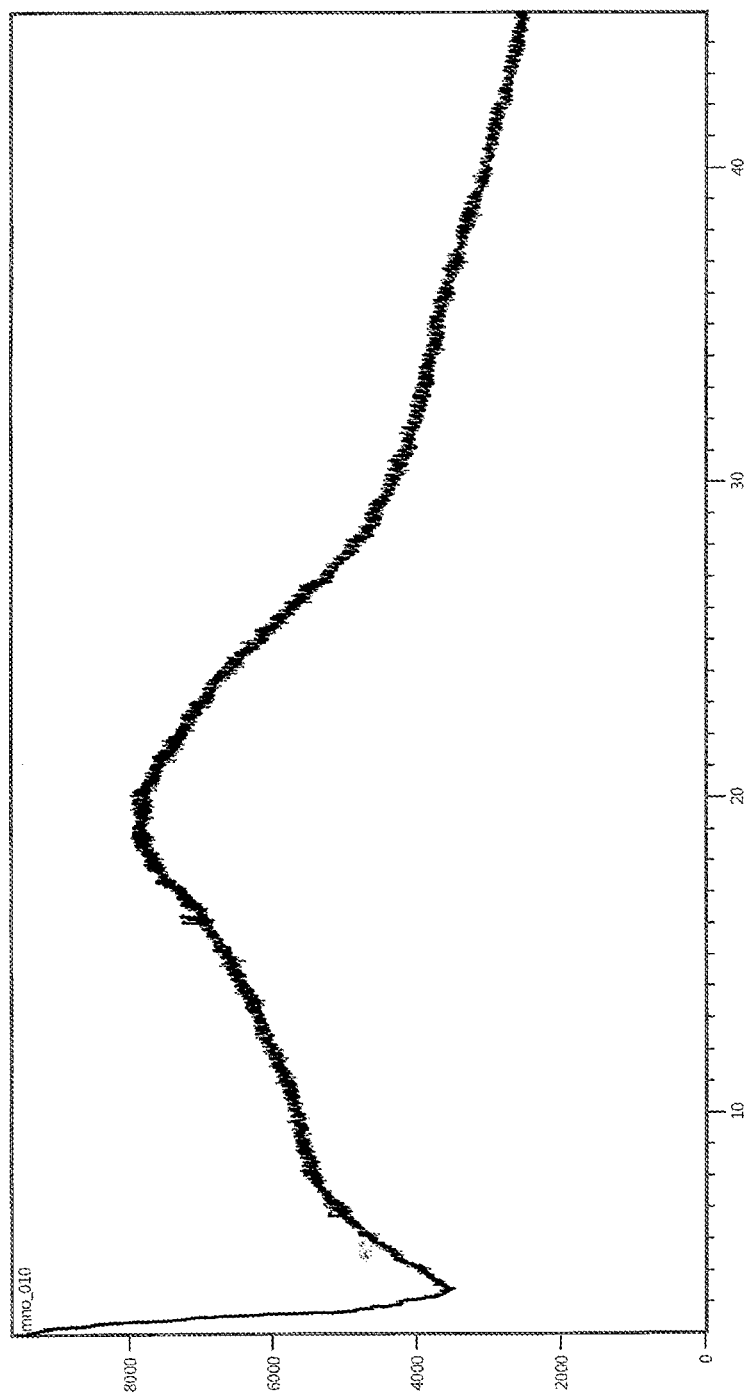
FIG. 9 shows a powder X-ray pattern of amorphous pullulan-supported nicotinamide-β-D-ribofuranoside chloride;
{x-axis: Position [° 2Theta] (Copper (Cu); y-axis: Counts), respectively}.

In another embodiment, the invention relates to crystalline thionicotinamide-2,3,5-tri-O-acetyl-β-D-ribofuranoside chloride of formula S-Ib characterized by a powder X-ray diffraction pattern as defined in FIG. 8.

The crystalline form may also be characterized by a powder X-ray diffraction pattern having peaks substantially as provided in Table 8, below, ±0.2 degrees two theta:

TABLE 8

| Pos. [°2Th.] | Height [cts] | FWHM Left [°2Th.] | d-spacing [Å] | Rel. Int. [%] |
|---|---|---|---|---|
| 4.7629 | 30989.72 | 0.0640 | 18.55331 | 48.42 |
| 9.5228 | 64007.27 | 0.0640 | 9.28763 | 100.00 |
| 11.2966 | 1385.84 | 0.1023 | 7.83301 | 2.17 |
| 12.0273 | 2951.19 | 0.0768 | 7.35867 | 4.61 |
| 13.1540 | 8423.38 | 0.1023 | 6.73083 | 13.16 |
| 13.8503 | 5372.95 | 0.0895 | 6.39396 | 8.39 |
| 14.0546 | 7164.81 | 0.0768 | 6.30149 | 11.19 |
| 14.2991 | 18424.71 | 0.0768 | 6.19426 | 28.79 |
| 14.5992 | 11231.60 | 0.1023 | 6.06762 | 17.55 |
| 15.3559 | 6070.71 | 0.1023 | 5.77026 | 9.48 |
| 15.5853 | 2908.67 | 0.1023 | 5.68586 | 4.54 |
| 16.2590 | 5787.38 | 0.0895 | 5.45174 | 9.04 |
| 16.8212 | 4919.45 | 0.1151 | 5.27078 | 7.69 |
| 17.4532 | 776.59 | 0.1279 | 5.08132 | 1.21 |
| 18.0942 | 13123.85 | 0.0895 | 4.90274 | 20.50 |
| 18.2901 | 1790.00 | 0.0640 | 4.85066 | 2.80 |
| 18.8734 | 15468.63 | 0.0895 | 4.70205 | 24.17 |
| 19.1009 | 31383.10 | 0.0895 | 4.64654 | 49.03 |
| 20.0535 | 4701.27 | 0.0768 | 4.42793 | 7.34 |
| 20.4586 | 3815.57 | 0.1663 | 4.34116 | 5.96 |
| 20.9713 | 273.54 | 0.1279 | 4.23616 | 0.43 |
| 21.6672 | 2891.86 | 0.0895 | 4.10167 | 4.52 |
| 22.1146 | 32720.12 | 0.0895 | 4.01969 | 51.12 |
| 22.2611 | 15800.38 | 0.0640 | 3.99355 | 24.69 |

TABLE 8-continued

| Pos. [°2Th.] | Height [cts] | FWHM Left [°2Th.] | d-spacing [Å] | Rel. Int. [%] |
|---|---|---|---|---|
| 22.7144 | 13549.10 | 0.1023 | 3.91487 | 21.17 |
| 23.1129 | 1558.49 | 0.1023 | 3.84828 | 2.43 |
| 23.6820 | 10056.44 | 0.1407 | 3.75707 | 15.71 |
| 23.9397 | 6079.45 | 0.0640 | 3.71720 | 9.50 |
| 24.1967 | 4206.54 | 0.1023 | 3.67830 | 6.57 |
| 25.0234 | 9998.71 | 0.1663 | 3.55862 | 15.62 |
| 25.6685 | 2351.72 | 0.1151 | 3.47064 | 3.67 |
| 26.4926 | 27607.33 | 0.1535 | 3.36452 | 43.13 |
| 27.3692 | 457.49 | 0.1023 | 3.25872 | 0.71 |
| 27.7114 | 2170.01 | 0.1023 | 3.21925 | 3.39 |
| 28.3345 | 1296.60 | 0.1023 | 3.14986 | 2.03 |
| 28.8200 | 12758.68 | 0.0640 | 3.09788 | 19.93 |
| 29.4666 | 1007.19 | 0.1279 | 3.03137 | 1.57 |
| 29.8579 | 3055.67 | 0.1663 | 2.99253 | 4.77 |
| 30.4167 | 1023.68 | 0.1535 | 2.93881 | 1.60 |
| 30.9424 | 1283.06 | 0.1023 | 2.89007 | 2.00 |
| 31.4066 | 2975.43 | 0.1151 | 2.84840 | 4.65 |
| 32.0957 | 2236.40 | 0.0895 | 2.78880 | 3.49 |
| 32.4438 | 1464.86 | 0.1023 | 2.75968 | 2.29 |
| 32.7074 | 3906.59 | 0.0895 | 2.73803 | 6.10 |
| 33.2688 | 2057.43 | 0.0768 | 2.69310 | 3.21 |
| 33.6753 | 6189.38 | 0.0624 | 2.65931 | 9.67 |
| 33.7459 | 6110.92 | 0.0512 | 2.65611 | 9.55 |
| 34.0335 | 2807.78 | 0.1151 | 2.63432 | 4.39 |
| 34.3454 | 3056.34 | 0.0640 | 2.61110 | 4.77 |
| 34.6680 | 3159.91 | 0.0895 | 2.58755 | 4.94 |

In another embodiment, the invention relates to a crystalline compound of formula Ia (O-Ia or S-Ia) or Ib (O-Ib or S-Ib) wherein the compound bears instead of the bromide ion or chloride anion another pharmaceutically acceptable anion such as an anion of sulfuric acid or phosphoric acid.

In another embodiment, the compound of formula Ia is obtainable by the method as defined in the first aspect.

In another embodiment, the compound of formula Ib is obtainable by the method as defined in the second aspect.

Use of Crystalline
(Thio)Nicotinamide-β-D-Ribofuranoside Bromide
and Pharmaceutically Acceptable Salts Thereof
(Fourth Aspect)

According to a fourth aspect, in one embodiment, the invention relates to the use of a (thio)nicotinamide-β-D-ribofuranoside bromide of formula Ia or of a (thio)nicotinamide-β-D-ribofuranoside chloride of formula Ib obtainable by a method as defined in the first or second aspect, or to the use of a (thio)nicotinamide-β-D-ribofuranoside bromide of formula Ia or (thio)nicotinamide-β-D-ribofuranoside chloride of formula Ib defined in the third aspect as nutritional supplement.

In another embodiment, the invention relates to the use of a (thio)nicotinamide-β-D-ribofuranoside chloride of formula Ib obtainable by a method defined in the second aspect, or to the use of a (thio)nicotinamide-β-D-ribofuranoside chloride of formula Ib defined in the third aspect as nutritional supplement, wherein the compound bears instead of the chloride anion as pharmaceutically acceptable anion another pharmaceutically acceptable anion, preferably an anion of sulfuric acid or phosphoric acid.

In another embodiment, the invention relates to a pharmaceutical composition comprising a (thio)nicotinamide-β-D-ribofuranoside bromide of formula Ia or (thio)nicotinamide-β-D-ribofuranoside chloride of formula Ib obtainable by a method defined in the first or second aspect or comprising a (thio)nicotinamide-β-D-ribofuranoside bromide of formula Ia or a (thio)nicotinamide-β-D-ribofuranoside chloride of formula Ib defined in the third aspect.

In another embodiment, the invention relates to a pharmaceutical composition comprising a (thio)nicotinamide-β-D-ribofuranoside chloride of formula Ib obtainable by a method defined in the second aspect, or comprising a (thio)nicotinamide-β-D-ribofuranoside chloride of formula Ib defined in the third aspect, wherein the compound bears instead of the chloride anion as pharmaceutically acceptable anion another pharmaceutically acceptable anion, preferably an anion of sulfuric acid or phosphoric acid.

In one embodiment, the (thio)nicotinamide-β-D-ribofuranoside bromide or chloride of formula Ia or Ib or the compound Ib bearing instead of the chloride anion as pharmaceutically acceptable anion another pharmaceutically acceptable anion, preferably an anion of sulfuric acid or phosphoric acid, are used in the prevention or treatment of diseases or conditions associated with the nicotinamide riboside kinase pathway or other pathways of NAD⁺ biosynthesis. These pathways are known in the art.

Method of Making a Supported
(Thio)Nicotinamide-β-D-Ribofuranoside Salt (Fifth
Aspect)

In a fifth aspect, the invention relates to a method of making a supported (thio)nicotinamide-β-D-ribofuranoside salt, wherein the (thio)nicotinamide-β-D-ribofuranoside salt is a salt as defined in the second aspect.

The method comprises a method as defined in the second aspect, and further comprises step (F):

(F) contacting a carrier with the (thio)nicotinamide-β-D-ribofuranoside salt, wherein the anion of the salt is a pharmaceutically acceptable anion, and one or more solvents.

Contacting as defined in step (F) may be simply performed by mixing.

Preferably, the (thio)nicotinamide-β-D-ribofuranoside salt is prepared according to the method as defined in the second aspect.

Preferably, the one or more solvents is/are water or contain water. In one embodiment, the educts are provided as aqueous solutions In order to isolate and solidify the target compound, the method further requires the removal of the one or more solvents.

Accordingly, the method further comprises step (G):

(G) removing the one or more solvents from the mixture obtained in step (F).

Removing the one or more solvents as defined in step (G) may be performed by distilling off the solvent, or preferably by lyophilisation.

The term "carrier" as used herein is synonymously used with the term "support".

Suitable carriers, may include, for example, calcium phosphate, silicon dioxide, magnesium stearate, talc, sugars, pullulan, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum metahydroxide, agar-agar, tragacanth, or mixtures thereof.

A preferred carrier is pullulan.

The term "pullulan" encompasses the various types of pullulans which are known in the field of pharmaceutical applications.

In one embodiment, the one or more solvent/solvents is/are selected from pharmaceutically acceptable solvents as are known in the art. In one embodiment, the solvent is water or comprises water.

At least in case of pullulan used as support, the supported (thio)nicotinamide-β-D-ribofuranoside salt is typically obtained as an optical clear, glass-like material or as a white solid. This solid typically is amorphous as may be shown by XRD analyses which do not provide for sharp peaks which would indicate the presence of crystals.

Composition Comprising a (Thio)Nicotinamide-β-D-Ribofuranoside Salt and a Carrier (Sixth Aspect)

According to a sixth aspect, the invention relates to a composition comprising a (thio)nicotinamide-β-D-ribofuranoside salt and a carrier.

Preferably, the (thio)nicotinamide-β-D-ribofuranoside salt is prepared according to the method as defined in the second aspect, and the composition is prepared according to the method as defined in the fifth aspect.

Further preferably, the carrier is a carrier as defined in the fifth aspect, preferably pullulan.

The composition defined in the sixth aspect may be used for the same applications or uses as defined in the fourth aspect.

Method of Making a Tri-O-Acyl-β-D-Ribofuranoside Bromide of Formula III (Seventh Aspect)

According to a seventh aspect, the invention relates to a method of making a tri-O-acyl-β-D-ribofuranoside bromide of formula III

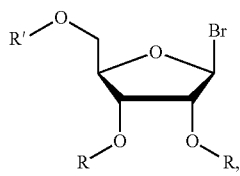

the method comprising step (α):
(α) subjecting a tetra-O-acyl-β-D-ribofuranose of formula II, wherein each R is independently selected from acyl,

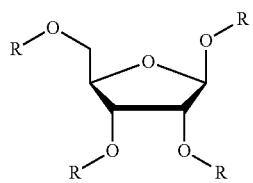

to hydrogen bromide in acetic acid.

Method of Removing Acyl Groups from (Thio) Nicotinamide-2,3,5-Tri-O-Acetyl-β-D-Ribofuranoside Bromide or Chloride (Eighth Aspect)

According to an eighth aspect, the invention relates to a method of removing the acyl groups from a compound of formula O-V, wherein each R is independently selected from acyl,

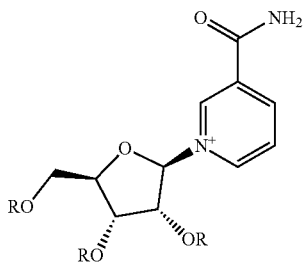

or of formula S-V

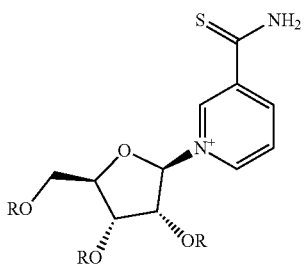

the method comprising step (i) or (ii):
(i) reacting the compound of formula O-V or formula S-V with hydrogen bromide in acetic acid;
(ii) reacting the compound of formula O-V or formula S-V with hydrogen chloride in methanol.

EXAMPLES

The following Examples further illustrate the present invention.

Example 1: Preparation of Nicotinamide-2,3,5-Tri-O-Acetyl-β-D-Ribofuranoside Bromide (a Compound of Formula O-Va)

274 g β-D-ribofuranose 1,2,3,5-tetraacetate were dissolved in 274 ml acetonitrile. 180 ml of hydrogen bromide in glacial acetic acid (concentration 33%) were added to the stirred solution while keeping the temperature between 0° C. and 5° C. Stirring was continued for further 15 minutes. 41 g of nicotinamide was added while stirring for another 15 minutes. A hot (70° C.) solution of 96 g nicotinamide in 700 ml acetonitrile was then added whereupon the mixture was cooled to about 0° C. to 5° C. Stirring was continued for 15 h, followed by filtration of the formed suspension. The filtrate was subjected to distillation. The obtained oily residue was diluted with acetone, resulting in crystallization of the title product. The title product was filtered and dried to give 167 g (43% yield) of an almost colorless product; Mp: 133-134° C.

$^1$H-NMR (400 MHZ, DMSO-d6): 2.09 (s, 6H), 2.13 (s, 3H) 4.45 (m, 2H, H5'), 4.69 (m, 1H, H4'), 5.43 (t, 1H, H3'), 5.62 (dd, 1H, H2'), 6.69 (d, 1H, H1'), 8.23 (s, 1H, NH), 8.41 (dd, 1H, H5), 8.74 (s, 1H, NH), 9.13 (d, 1H, H4), 9.28 (d, 1H, H6), 9.49 (s, 1H, H2);

$^{13}$C-NMR (100 MHz, DMSO-d6): 20.3, 20.4, 20.5, 62.1 (C5'), 68.7 (C3'), 75.3 (C2'), 81.8 (C4'), 97.2 (C1'), 128.1

(C5), 133.9 (C3), 141.2 (C2), 143.1 (C6), 145.5 (C4), 162.7 (CONH2), 169.2, 169.4, 170.1.

Example 2: Preparation of Nicotinamide-β-D-Ribofuranoside Bromide of Formula O-Ia 167 g of the product obtained in Example 1 were dissolved in 870 ml methanol. 135 ml of hydrogen bromide in acetic acid (concentration 33%) were then added to the stirred solution while keeping the temperature between 5° C. to 10° C. The resulting mixture was stirred for two days at 20° C. wherein the product started crystallizing. The formed crystals were filtered off, washed with isopropanol and dried. The title compound was obtained in a yield of 77 g (63%) as a pale yellow crystalline powder; Mp: 118-119° C.

$^1$H-NMR (400 MHZ, $D_2O$): 3.83 (dd, 1H, H5'), 3.98 (dd, 1H, H5'), 4.29 (t, 1H, H3'), 4.39-4.48 (m, 2H, H4', H2'), 6.18 (d, 1H, H1'), 8.22 (t, 1H, H5), 8.91 (d, 1H, H4), 9.20 (d, 1H, H6), 9.52 (s, 1H, H2);

$^{13}$C-NMR (100 MHZ, $D_2O$): 60.0 (C5'), 69.5 (C3'), 77.2 (C2'), 87.5 (C4'), 99.7 (C1'), 128.5 (C5), 133.7 (C3), 140.2 (C2), 142.5 (C6), 145.5 (C4), 165.6 (CONH2).

Example 3: Preparation of Nicotinamide-β-D-Ribofuranoside Chloride of Formula O-Ib 25 g of the product obtained in Example 2 were dissolved in 140 ml water and 140 g of ion exchange resin Amberlite IRA-402 (Cl-Form) were added and stirred for two hours. The resin was removed by filtration and washed with 140 ml water. To the filtrate were added 105 g of ion exchange resin, again stirred for two hours, filtered and washed with 40 ml water. This exchange was repeated further two times using 105 g of ion exchanger each. The final filtrate was evaporated to give 21.8 g of a clear, pale yellow resin. This resin was dissolved in a hot mixture of 100 ml ethanol and 100 ml methanol. The crystals obtained after cooling in an ice bath were filtered, washed with isopropanol and dried to give 12.8 g (59%) of the title compound as colorless crystals. The bromide content was below 0.1%. Mp: 123-124° C.

$^1$H-NMR (400 MHZ, $D_2O$): 3.84 (dd, 1H, H5'), 3.98 (dd, 1H, H5'), 4.30 (t, 1H, H3'), 4.40-4.47 (m, 2H, H4', H2'), 6.19 (d, 1H, H1'), 8.22 (t, 1H, H5), 8.92 (d, 1H, H4), 9.21 (d, 1H, H6), 9.54 (s, 1H, H2);

$^{13}$C-NMR (100 MHZ, $D_2O$): 60.3 (C5'), 69.8 (C3'), 77.5 (C2'), 87.7 (C4'), 99.9 (C1'), 128.5 (C5), 134.0 (C3), 140.4 (C2), 142.7 (C6), 145.7 (C4), 165.8 (CONH2).

Example 4: Preparation of Nicotinamide-β-D-Ribofuranoside Chloride/Bromide (Mixed Salt of Formula O-Ib/O-Ia)

10 g of the intermediate product obtained in Example 1 were dissolved in 50 ml methanol. 15 ml of hydrogen chloride in ethanol (concentration 6 moles per L) were then added to the stirred solution while keeping the temperature between 5° C. to 10° C. The resulting mixture was stirred overnight at 20° C. whereby the product crystallized. The crystals were filtered off, washed with isopropanol and dried. The mixture of the title compounds was obtained in a yield of 4.6 g (73%). The ratio of chloride to bromide was about 3:1.

Example 5: Preparation of Thionicotinamide-2,3,5-Tri-O-Acetyl-β-D-Ribofuranoside Bromide (a Compound of Formula S-Va)

30 g β-D-ribofuranose 1,2,3,5-tetraacetate were dissolved in 30 ml acetonitrile. 19.8 ml of hydrogen bromide in glacial acetic acid (concentration 33%) were added to the stirred solution while keeping the temperature between 0° C. and 5° C. Stirring was continued for further 15 minutes. 4.5 g of thionicotinamide was added while stirring for another 15 minutes. A hot (65° C.) solution of 12 g thionicotinamide in 510 ml acetonitrile was then added whereupon the mixture was cooled to about 0° C. to 5° C. Stirring was continued for 15 h at 0° C., followed by filtration of the formed suspension. The filtrate was subjected to distillation. The obtained oily residue was diluted with a mixture (1:1) of ethanol and isopropanol, resulting in crystallization of the title product which was filtered and dried to give 22 g (50% yield) of yellow crystalline powder. Mp: 134° C.

$^1$H-NMR (400 MHZ, DMSO-d6): 2.06 (s, 3H), 2.09 (s, 3H), 2.14 (s, 3H) 4.43 (m, 2H, H5'), 4.70 (m, 1H, H4'), 5.43 (t, 1H, H3'), 5.63 (dd, 1H, H2'), 6.68 (d, 1H, H1'), 8.31 (dd, 1H, H5), 8.99 (d, 1H, H4), 9.20 (d, 1H, H6), 9.49 (s, 1H, H2), 10.30 (s, 1H, NH), 10.66 (s, 1H, NH);

$^{13}$C-NMR (100 MHZ, DMSO-d6): 20.3, 20.4, 20.6, 62.3 (C5'), 68.9 (C3'), 75.3 (C2'), 82.0 (C4'), 97.1 (C1'), 127.6 (C5), 138.6 (C3), 140.4 (C2), 142.3 (C6), 144.2 (C4), 192.5 (CSNH2), 169.2, 169.4, 170.0.

Example 6: Preparation of Thionicotinamide-β-D-Ribofuranoside Bromide of Formula S-Ia 18.6 g of the product obtained in Example 5 were dissolved in 110 ml methanol. 14 ml of hydrogen bromide in acetic acid (concentration 33%) were then added to the stirred solution while keeping the temperature between 5° C. to 10° C. The resulting mixture was stirred for two days at 20° C. wherein the product started crystallizing. The suspension was cooled to 0° C. and the yellow crystals were filtered off, washed with isopropanol and dried. The title compound was obtained in a yield of 9.3 g (68%). Mp: 123° C.

$^1$H-NMR (400 MHZ, $D_2O$): 3.84 (dd, 1H, H5'), 3.99 (dd, 1H, H5'), 4.31 (t, 1H, H3'), 4.38-4.50 (m, 2H, H4', H2'), 6.18 (d, 1H, H1'), 8.15 (t, 1H, H5), 8.83 (d, 1H, H4), 9.13 (d, 1H, H6), 9.60 (s, 1H, H2);

$^{13}$C-NMR (100 MHZ, $D_2O$): 60.2 (C5'), 69.7 (C3'), 77.4 (C2'), 87.5 (C4'), 100.0 (C1'), 128.0 (C5), 139.6 (C3), 139.9 (C2), 141.6 (C6), 143.8 (C4), 194.5 (CSNH2).

Example 7: Preparation of Nicotinamide-2,3,5-Tri-O-Acetyl-β-D-Ribofuranoside Bromide/Chloride (a Mixed Salt of Formula O-Va/O-Vb)

274 g β-D-ribofuranose 1,2,3,5-tetraacetate were dissolved in 274 ml acetonitrile. 180 ml of hydrogen bromide in glacial acetic acid (concentration 33%) were then added to the stirred solution while keeping the temperature between 0° C. to 5° C. Stirring was continued for further 15 minutes. 41 g of nicotinamide was added while stirring for another 15 minutes. A hot (55° C.) solution of 96 g nicotinamide in 1,800 ml acetonitrile was then added whereupon the mixture was cooled to about 0° C. to 5° C. Stirring was continued for 15 h, followed by filtration of the formed suspension. To the filtrate were added 3,600 g of strongly basic anion exchange resin Amberlite IRA-402 in the chloride form which had been washed with acetonitrile before use to remove humidity. The resin was stirred for three hours and then filtered off. The filtrate was subjected to distillation. The obtained oily residue was diluted with acetone, resulting in crystallization of the title product. The title product was filtered and dried to give 147 g (41% yield) of an almost colorless product. The ratio of chloride to bromide was about 8:1. Mp: 141° C.

$^1$H-NMR (400 MHZ, DMSO-d6): 2.10 (s, 6H), 2.14 (s, 3H) 4.47 (m, 2H, H5'), 4.69 (m, 1H, H4'), 5.45 (t, 1H, H3'), 5.65 (dd, 1H, H2'), 6.70 (d, 1H, H1'), 8.23 (s, 1H, NH), 8.40 (dd, 1H, H5), 9.07 (s, 1H, NH), 9.13 (d, 1H, H4), 9.26 (d, 1H, H6), 9.31 (s, 1H, H6), 9.63 (s, 1H, H2);

$^{13}$C-NMR (100 MHZ, DMSO-d6): 20.8, 20.9, 21.0, 62.7 (C5'), 69.2 (C3'), 75.7 (C2'), 82.3 (C4'), 97.2 (C1'), 128.5 (C5), 134.4 (C3), 141.9 (C2), 143.6 (C6), 146.2 (C4), 163.1 (CONH2), 169.7, 169.9, 170.6.

Example 8: Preparation of Nicotinamide-β-D-Ribofuranoside Chloride of Formula O-Ib by Deprotection of Nicotinamide-2,3,5-Tri-O-Acetyl-β-D-Ribofuranoside Chloride of Formula O-Vb General procedure: Nicotinamide-tri-O-acetyl-β-D-ribofuranoside chloride was dissolved in methanol (4.9 mL/g). Afterwards 2 equivalents of a solution of hydrochloric acid in ethanol (7.6 N) was added dropwise and the reaction mixture was stirred for 4 h at r.t. The crude product was filtered, washed with isopropyl alcohol and methanol and dried over 48 hours under reduced pressure to yield the pure nicotinamide-β-D-ribofuranoside chloride as a white solid (49-64%).

a) Nicotinamide-tri-O-acetyl-β-D-ribofuranoside chloride=1.95 kg (4.679 mol) in 9.5 L MeOH
7.6 N HCl (9.357 mol, 2.0 eq., 1.231 L)
4 h at r.t.
1*2 L IPA, 1*2 L MeOH
Nicotinamide-β-D-ribofuranoside chloride=672 g (2.312 mol, 49%)

b) Nicotinamide-tri-O-acetyl-beta-D-ribofuranoside chloride=1.70 kg (4.079 mol) in 8.5 L MeOH
7.6 N HCl (2.0 eq., 8.157 mol, 1.073 L)
4 h at r.t.
1*2 L IPA, 1*2 L MeOH
Nicotinamide-β-D-ribofuranoside chloride=757 g (2.604 mol, 64%)
Purity (HPLC) 99.3 area-%
Impurity (Nicotinamide) 0.3%

$^1$H-NMR (400 MHz, D$_2$O) δ ppm 3.85 (dd, J=13.0, 3.5 Hz, 1H) 3.96-4.03 (m, 1H) 4.29-4.34 (m, 1H) 4.40-4.50 (m, 2H) 6.21 (d, J=4.6 Hz, 1H) 8.24 (t, J=6.8 Hz, 1H) 8.94 (d, J=8.3 Hz, 1H) 9.23 (d, J=6.1 Hz, 1H) 9.55 (s, 1H).

Examples 9 to 12: Preparation of Nicotinamide-β-D-Ribofuranoside and Nicotin-Amide-2,3,5-Tri-O-Acetyl-β-D-Ribofuranoside Sulfate and Phosphate Salts Using Ion Exchange Resins Activation of the ion-exchange resin: 40 g Ambersep® 900 hydroxide form (The Dow Chemical Company) were rinsed with 250 mL 10% H$_2$SO$_4$ or 10% H$_3$PO$_4$ aqueous solution and washed with water until the pH-value of the washing solution remained constant.

General procedure: A solution of nicotinamide-β-D-ribofuranoside bromide of formula O-Ia or nicotinamide-2,3,5-tri-O-acetyl-β-D-ribofuranoside bromide of formula O-Va prepared according to the methods of the invention in water was filtered through the activated ion-exchange resin and lyophilized to afford the corresponding sulfate or dihydrogen phosphate as a solid:

Example 9: 4.0 g nicotinamide-tri-O-acetyl-β-D-ribofuranoside bromide (8.67 mmol; 1 eq) was dissolved in 15 mL water and filtered through 120 g H$_2$SO$_4$-activated ion exchange resin, washed with 400 ml water and lyophilized to afford 3.71 g nicotinamide-tri-O-acetyl-β-D-ribofuranoside sulfate (7.77 mmol, 90%) as a yellow solid.

Bromide content (IC): 0.0%; Sulfate content (IC): 6.9%; $^1$H-NMR (400 MHZ, D$_2$O) δ ppm 2.11 (s, 3H) 2.15 (s, 3H) 2.18 (s, 3H) 4.47-4.60 (m, 2H) 4.84-4.98 (m, 1H) 5.47 (t, J=5.4 Hz, 1H) 5.59 (dd, J=5.4, 3.9 Hz, 1H) 6.61 (d, J=3.8 Hz, 1H) 8.30 (dd, J=8.0, 6.4 Hz, 1H) 9.02 (dt, J=8.1, 1.4 Hz, 1H) 9.22 (ddd, J=6.2, 1.5 Hz, 1H) 9.46 (s, 1H).

Example 10: 1.3 g nicotinamide-tri-O-acetyl-β-D-ribofuranoside bromide (2.82 mmol; 1 eq) was dissolved in 5 mL water and filtered through 40 g H$_3$PO$_4$-activated ion exchange resin, washed with 150 ml water and lyophilized to afford 1.27 g nicotinamide-tri-O-acetyl-β-D-ribofuranoside dihydrogen phosphate (2.66 mmol, 94%) as a white solid.

Bromide content (IC): 0.0%; Phosphate content (IC): 19.1% $^1$H-NMR (400 MHZ, D$_2$O) δ ppm 2.10 (s, 3H) 2.14 (s, 3H) 2.17 (s, 3H) 4.45-4.61 (m, 2H) 4.81-4.97 (m, 1H) 5.46 (t, J=5.4 Hz, 1H) 5.57 (dd, J=5.3, 4.0 Hz, 1H) 6.60 (d, J=4.1 Hz, 1H) 8.29 (t, J=6.7 Hz, 1H) 8.94-9.08 (m, 1H) 9.21 (d, J=6.2 Hz, 1H) 9.45 (s, 1H).

Example 11: 1.3 g nicotinamide-β-D-ribofuranosidebromide (3.88 mmol; 1 eq) was dissolved in 5 mL water and filtered through 40 g H$_2$SO$_4$-activated ion exchange resin, washed with 150 ml water and lyophilized to afford 1.27 g nicotinamide-β-D-ribofuranoside sulfate (3.62 mmol, 93%) as a white solid.

Bromide content (IC): 0.0%; Sulfate content (IC): 13.0% $^1$H-NMR (400 MHZ, D$_2$O) δ ppm 3.83 (dd, J=13.0, 3.6 Hz, 1H) 3.91-4.02 (m, 1H) 4.25-4.34 (m, 1H) 4.36-4.41 (m, 1H) 4.46 (t, J=4.7 Hz, 1H) 6.20 (d, J=4.4 Hz, 1H) 8.24 (t, J=6.9 Hz, 1H) 8.93 (d, J=8.3 Hz, 1H) 9.23 (d, J=6.2 Hz, 1H) 9.53 (s, 1H).

Example 12: 1.3 g nicotinamide-β-D-ribofuranoside bromide (3.88 mmol; 1 eq) was dissolved in 5 mL water and filtered through 40 g H$_3$PO$_4$-activated ion exchange resin, washed with 150 ml water and lyophilized to afford 1.42 g nicotinamide-β-D-ribofuranoside dihydrogen phosphate (4.16 mmol, 104%; containing 10% water) as a white solid.

Bromide content (IC): 0.0%; Phosphate content (IC): 20.8% $^1$H NMR (400 MHZ, D$_2$O) δ ppm 3.81 (dd, J=13.0, 3.6 Hz, 1H) 3.96 (dd, J=13.0, 2.8 Hz, 1H) 4.21-4.33 (m, 1H) 4.39 (d, J=3.9 Hz, 1H) 4.43 (t, J=4.7 Hz, 1H) 6.16 (d, J=4.6 Hz, 1H) 8.20 (t, J=6.9 Hz, 1H) 8.89 (d, J=7.7 Hz, 1H) 9.19 (d, J=6.3 Hz, 1H) 9.51 (s, 1H).

Example 13 to 17: Compositions with Pullulan

Examples 13 and 14: Stock solutions of pullulan and nicotinamide β-D-ribofuranoside chloride prepared according to the methods of the invention were mixed in the following ratios:

Example 13: 1.8 mL of an aqueous pullulan solution (120 mg/ml) was mixed with 0.050 mL of an aqueous solution of nicotinamide β-D-ribofuranoside chloride (200 mg/mL)

Example 14: 4 mL of an aqueous pullulan solution (120 mg/ml) was mixed with 0.050 mL of an aqueous solution of nicotinamide β-D-ribofuranoside chloride (200 mg/mL); from both solutions were 0.4 mL aliquots pipetted on a solid surface and let dried at 21° C. and 30% room humidity for 15 hours to obtain amorphous, glassy, hard lens-shaped pullulan nicotinamide β-D-ribofuranoside chloride tablet.

Examples 15 to 17: Nicotinamide β-D-ribofuranoside chloride was added to a solution of pullulan (5 mg/mL) in water. The reaction mixture was homogenized with ultrasound for 5 minutes and lyophilized overnight to yield the specific nicotinamide β-D-ribofuranoside chloride-pullulan-complexes as white solids. The white solids were amorphous as was shown by XRD analyses due to the absence of sharp diffraction peaks. Example 15:250 mg pullulan; 250 mg nicotinamide β-D-ribofuranoside chloride. Example 16:500 mg pullulan; 250 mg nicotinamide β-D-ribofuranoside chloride. Example 17:1.2 g pullulan; 250 mg nicotinamide β-D-ribofuranoside chloride.

Example 18: Preparation of Thionicotinamide-β-D-Ribofuranoside Chloride (a Compound of Formula S-Ib)

15 g of thionicotinamide-β-D-ribofuranoside bromide S-Ia from Example 6 were dissolved in 80 ml water. 66 g of ion exchange resin Amberlite IRA-402 (Cl-Form) were added to the orange-yellow solution and stirred for half an hour. The resin was removed by filtration and washed with 150 ml water in three portions. To the filtrate were added 66 g of ion exchange resin, again stirred for half an hour, filtered and washed with 150 ml water in three portions. This exchange was repeated further three times using 66 g of ion exchanger each. The final filtrate was evaporated to give 14.7 g of a clear, orange-yellow oil. This oil was dissolved in 30 ml methanol and put in the refrigerator, whereby some crystals formed overnight. The next day crystallization was completed by stirring in an ice bath and diluting the thick yellow suspension with a mixture of 45 ml methanol and 75 ml ethanol. The product was filtered, washed with ethanol several times and dried to give 6.7 g (51%) of the title compound as bright yellow crystals. The bromide content (IC) was below 0.1%. Mp: 117° C.

From the mother liquor further 3.63 g (28%) of yellow crystals were isolated. Mp: 116° C.

$^1$H-NMR (400 MHZ, D$_2$O): 3.85 (dd, 1H, H5'), 3.99 (dd, 1H, H5'), 4.31 (t, 1H, H3'), 4.40-4.50 (m, 2H, H4', H2'), 6.18 (d, 1H, H1'), 8.16 (t, 1H, H5), 8.84 (d, 1H, H4), 9.14 (d, 1H, H6), 9.61 (s, 1H, H2);

$^{13}$C-NMR (100 MHZ, D$_2$O): 60.2 (C5'), 69.7 (C3'), 77.4 (C2'), 87.6 (C4'), 100.0 (C1'), 128.0 (C5), 139.6 (C3), 139.9 (C2), 141.7 (C6), 143.9 (C4), 194.6 (CSNH2).

Example 19: Preparation of Thionicotinamide-2,3,5-Tri-O-Acetyl-β-D-Ribofuranoside Chloride (a Compound of Formula S-Vb)

10 g of thionicotinamide-2,3,5-tri-O-acetyl-β-D-ribofuranoside bromide S-Va from Example 5 were dissolved in 50 ml water. 44 g of ion exchange resin Amberlite IRA-402 (Cl-Form) were added to the orange-yellow solution and stirred for half an hour. The resin was removed by filtration and washed with 100 ml water in two portions. To the filtrate were added 44 g of ion exchange resin, again stirred for half an hour, filtered and washed with 100 ml water in two portions. This exchange was repeated further three times using 44 g of ion exchanger each. The final filtrate was evaporated to give 9.6 g of an orange-yellow resin. Most of the resin dissolved in 20 ml ethanol and soon after a bright yellow precipitate was formed. The rest of the resin crystallized while stirring with further 30 ml ethanol for one hour at 40° C. The suspension was stored overnight at 5° C. 20 ml isopropanol were added and the yellow suspension stirred once more for an hour at 5° C. The product was filtered, washed several times with isopropanol and dried to give 8.8 g (90%) of the title compound as a yellow crystalline powder. The bromide content (IC) was below 0.1%. Mp: 138° C.

$^1$H-NMR (400 MHZ, DMSO-d6): 2.07 (s, 3H), 2.11 (s, 3H), 2.14 (s, 3H) 4.47 (m, 2H, H5'), 4.70 (m, 1H, H4'), 5.47 (t, 1H, H3'), 5.69 (dd, 1H, H2'), 6.71 (d, 1H, H1'), 8.31 (dd, 1H, H5), 9.14 (d, 1H, H4), 9.27 (d, 1H, H6), 9.63 (s, 1H, H2), 10.70 (s, 1H, NH), 10.88 (s, 1H, NH);

$^{13}$C-NMR (100 MHZ, DMSO-d6): 20.8, 20.9, 21.1, 62.9 (C5'), 69.6 (C3'), 75.7 (C2'), 82.6 (C4'), 97.6 (C1'), 127.9 (C5), 138.8 (C3), 141.0 (C2), 142.8 (C6), 145.3 (C4), 192.7 (CSNH2), 169.7, 169.9, 170.5.

What is claimed is:

1. A crystalline nicotinamide-2,3,5-tri-O-acetyl-β-D-ribofuranoside bromide of formula O-Va:

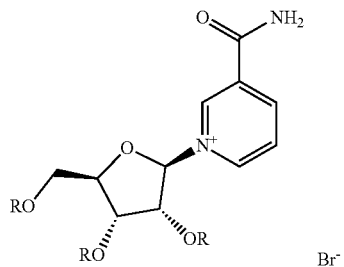

wherein R is acetyl, characterized by a powder X-ray diffraction pattern substantially as defined in FIG. 1; or a crystalline nicotinamide-β-D-ribofuranoside bromide of formula O-Ia:

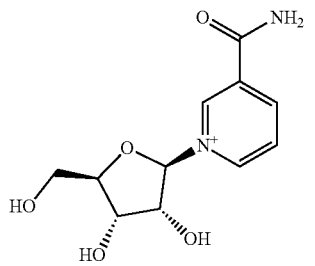

characterized by a powder X-ray diffraction pattern substantially as defined in FIG. 2; or a crystalline nicotinamide-β-D-ribofuranoside chloride of formula O-Ib:

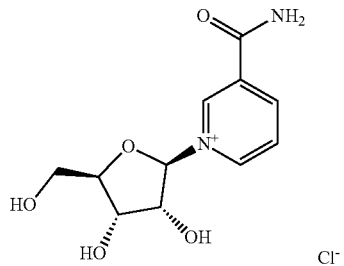

characterized by a powder X-ray diffraction pattern as defined in FIG. 4; or a crystalline thionicotinamide-2,3,5-tri-O-acetyl-β-D-ribofuranoside bromide of formula S-Va:

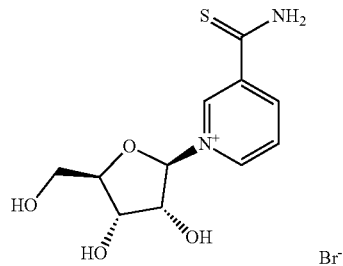

wherein R is acetyl, characterized by a powder X-ray diffraction pattern substantially as defined in FIG. 5; or a crystalline thionicotinamide-β-D-ribofuranoside bromide of formula S-Ia:

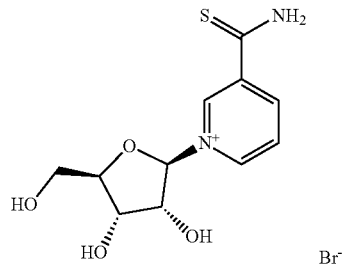

characterized by a powder X-ray diffraction pattern substantially as defined in FIG. 6; or a crystalline thionicotinamide-β-D-ribofuranoside chloride of formula S-Ib:

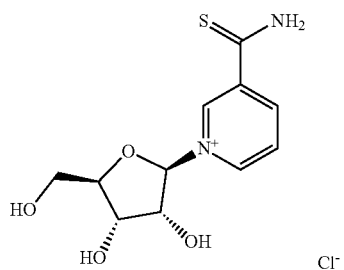 [SMILES: NC(=S)c1ccc[n+]([C@@H]2O[C@H](CO)[C@@H](O)[C@H]2O)c1 ; [Br-]]

characterized by a powder X-ray diffraction pattern substantially as defined in FIG. 7; or a crystalline thionicotinamide-2,3,5-tri-O-acetyl-β-D-ribofuranoside chloride of formula S-Vb:

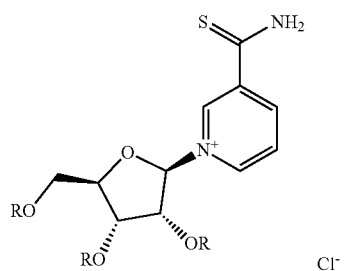

wherein R is acetyl, characterized by a powder X-ray diffraction pattern substantially as defined in FIG. 8.

2. A composition comprising the crystalline salt of claim 1, wherein the composition is a nutritional supplement or a pharmaceutical composition.

* * * * *